US008507540B2

(12) United States Patent
Keum et al.

(10) Patent No.: US 8,507,540 B2
(45) Date of Patent: Aug. 13, 2013

(54) OXAZOLIDINONE DERIVATIVES CONTAINING NEW BICYCLIC GROUP, HAVING ANTIBACTERIAL ACTIVITY, AND METHOD FOR TREATING PATHOGENIC BACTERIAL INFECTIONS USING THE SAME

(75) Inventors: Gyo-Chang Keum, Seoul (KR); Eunice Eun-Kyeong Kim, Seoul (KR); Ae-Nim Pae, Seoul (KR); Kyung-Il Choi, Seoul (KR); Soon-Bang Kang, Seoul (KR); Seon-Hee Seo, Seoul (KR); Deepak Bhattaral, Seoul (KR); Ju-Hyeon Lee, Seoul (KR)

(73) Assignee: Korean Institute of Science and Technology, Seoul (KR)

( * ) Notice: Subject to any disclaimer, the term of this patent is extended or adjusted under 35 U.S.C. 154(b) by 69 days.

(21) Appl. No.: 13/314,706

(22) Filed: Dec. 8, 2011

(65) Prior Publication Data

US 2013/0012554 A1 Jan. 10, 2013

(30) Foreign Application Priority Data

Jul. 5, 2011 (KR) ........................ 10-2011-0066569

(51) Int. Cl.
*A61K 31/422* (2006.01)
*A61P 31/04* (2006.01)
*C07D 413/14* (2006.01)

(52) U.S. Cl.
USPC .......................................... 514/376; 548/231

(58) Field of Classification Search
None
See application file for complete search history.

(56) References Cited

U.S. PATENT DOCUMENTS 5,254,577 A * 10/1993 Carlson et al. ................. 514/376

FOREIGN PATENT DOCUMENTS

| KR | 10-0463771 | 5/2005 |
| WO | 95/07271 | 3/1995 |
| WO | 96-35691 | 11/1996 |

OTHER PUBLICATIONS

Lisa A. Collins et al., "Microplate Alamar Blue Assay versus BACTEC 460 System for High-Throughput Screening of Compounds against *Mycobacterium tuberculosis* and *Mycobacterium avium*", Antimicrobial Agents and Chemotherapy, vol. 41, No. 5, May 1997, 7 pp.
Dean L. Shinabarger et al., "Mechanism of Action of Oxazolidinones: Effects of Linezolid and Eperezolid on Translation Reactions", Antimicrobial Agents and Chemotherapy, vol. 41, No. 10, Oct. 1997, 6 pp.
Cecilia Farre et al., "Port-a-Patch and Patchliner: High Fidelity Electrophysiology for Secondary Screening and Safety Pharmacology", Combinational Chemistry and High Throughput Screening, 2009 Bentham Science Publishers Ltd., pp. 24-37.
Joseph A. Ippolito et al., "Crystal Structure of the Oxazolidinone Antibiotic Linezolid Bound to the 50S Ribosomal Subunit", J. Med. Chem., May 22, 2008, vol. 51, pp. 3353-3356.
Walter A. Korfmacher et al., "Development of an Automated Mass Spectrometry System for the Quantitative Analysis of Liver Microsomal Incubation Samples: a Tool for Rapid Screening of New Compounds for Metabolic Stability", Rapid Communications in Mass Spectrometry, 1999, Vo. 13, pp. 901-907.

* cited by examiner

*Primary Examiner* — Kamal Saeed
(74) *Attorney, Agent, or Firm* — Staas & Halsey LLP

(57) ABSTRACT

The present invention relates to oxazolidinone derivatives containing new bicyclic group, having antibacterial activity, or a pharmaceutically acceptable salt thereof, a method for preparing the same, an antibacterial composition comprising the oxazolidinone derivative or a pharmaceutically acceptable salt thereof as an active ingredient, and a method for treating an infectious disease caused by pathogen using the same. The oxazolidinone derivative or a pharmaceutically acceptable salt thereof may exhibit excellent antibacterial activity against gram positive bacteria including various resistant strains.

13 Claims, No Drawings

OXAZOLIDINONE DERIVATIVES CONTAINING NEW BICYCLIC GROUP, HAVING ANTIBACTERIAL ACTIVITY, AND METHOD FOR TREATING PATHOGENIC BACTERIAL INFECTIONS USING THE SAME

CROSS REFERENCE TO RELATED APPLICATIONS

This application claims the benefit of Korean Application No. 10-2011-0066569, filed Jul. 5, 2011, the disclosure of which is incorporated herein by reference.

BACKGROUND OF THE INVENTION (a) Field of the Invention

The present invention relates to novel oxazolidinone derivatives having antibacterial activity, or a pharmaceutically acceptable salt thereof, a method for preparing the same, an antibacterial composition comprising the oxazolidinone derivative or a pharmaceutically acceptable salt thereof as an active ingredient, and a method for treating an infectious disease caused by pathogen using the same.

(b) Description of the Related Art

Since penicillin was discovered by Fleming at 1929, a lot of studies have been progressed on betalactam, aminoglucoside, macrolide, quinolone, tetracycline, glycopeptides antibiotics. When penicillin was first discovered by Fleming, it was called as a magical drug that can kill most bacteria. However, not long after the use, resistant bacteria was found from colon bacillus, and as strains having resistance to the antibiotics are continuously developed, resistant strains so-called super bacteria that does not respond to any antibiotics continuously appear.

Currently, more various kinds of antibiotics are developed, while resistance to the antibiotics is observed from various kinds of strains. As the application range of antibiotics is broadened, bacteria itself cause mutation more variously and thus resistance is increasing explosively. And, rapid increase of antibiotics raises resistance problem in a more complicated way than before. In practice, strains such as methicillin-resistant *Staphylococcus Aureus* (MRSA), methicillin-resistant *Staphylococcus Epidermidis* (MRSE), penicillin-resistant *Streptococcus pneumonia*, quinolone-resistant *Staphylococcus Aureus* (QRSA), vancomycin-resistant *Staphylococcus Aureus* (VRSA), vancomycin-resistant Enterococci (VRE), and multi-drug resistant *Mycobacterium tuberculosis* show resistance to most antibiotics in use. Thus, studies and developments of new antibiotics are required, and to overcome resistant strain problem, studies on antibiotics having new structure and mechanism of action are urgently demanded.

At 1987, Dupont company discovered that Dup-105 and Dup-721 having an oxazolidinone structure have antibacterial effects, and as results of researches on the pharmaceutical efficacy, disclosed that they have antibacterial activities against gram positive bacteria including resistant strains. Through studies on the structure-activity of the compounds of this type since then, at April, 2000, antibiotics of a new structure, i.e., a compound linezolid (Zyvox®) was developed by Pharmacia & Upjohn company 40 years after quinolone type antibiotics (WO 95/07271).

At 1997, it was known that Pharmacia's linezolid selectively binds to 50S ribosomal subunit adjacent to the interface of 30S ribosomal subunit (*Antimicrob Agents Chemother* 1997, 41:2132-2136), and the crystal structure wherein linezolid is binded to the 50S ribosomal subunit was reported (*J. Med. Chem.*, 2008, 51, 3353-356). Although it is known that the oxazolidinone antibiotics manifests excellent pharmacokinetic property through new mechanism of action, which is different from those of the existing antibiotics, and is now in the position of a last resort to treat gram positive bacterial infection generated by MRSA or VRE, linezolid resistance is being reported among the gram positive bacteria.

Accordingly, there is a need for development of novel compounds having excellent efficacy against a broad range of antibiotics-resistant strains through modification of the chemical structure of oxazolidinone antibiotics.

SUMMARY OF THE INVENTION

In order to solve the problems of the prior art, the present invention provides novel oxazolidinone derivatives having excellent antibacterial activity against gram positive bacteria including various resistant strains, or a pharmaceutically acceptable salt thereof, a method for preparing the same, an antibacterial composition comprising the oxazolidinone derivative or a pharmaceutically acceptable salt thereof as an active ingredient, and a method for treating an infectious disease caused by pathogen using the same.

DETAILED DESCRIPTION OF THE EMBODIMENTS

As the results of studies on the synthesis of novel oxazolidinone derivatives having excellent antibacterial activity against a broad range of strains showing resistance to the existing antibiotics, the inventors confirmed that oxazolidinone derivative containing a cyclopenta[c]pyrrolyl group exhibit remarkably improved antibacterial activity against gram positive bacteria including various resistant strains, and completed the invention.

According to one embodiment of the present invention, an oxazolidinone derivative containing a cyclopenta[c]pyrrolylphenyl group, and represented by the following Chemical Formula 1, or a pharmaceutically acceptable salt thereof is provided:

[Chemical Formula 1]

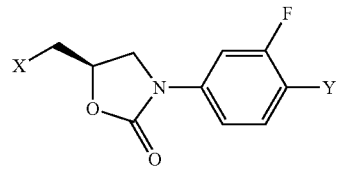

wherein,

X is acetamido (-NHAc) group or 1H-1,2,3-triazol-1-yl group,

Y is

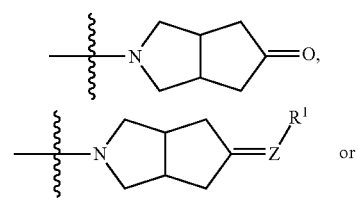

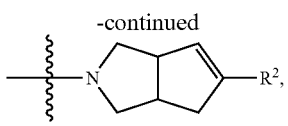

Z is nitrogen or carbon,
R$^1$ is hydroxyl group (—OH), C$_1$-C$_7$ alkyloxy group, benzyloxy group, cyano group (—CN), or C$_1$-C$_7$ alkyloxycarbonyl group,
R$^2$ is cyano group or cyanomethyl group.
Preferably, when the X is acetamido (-NHAc) group, Y is

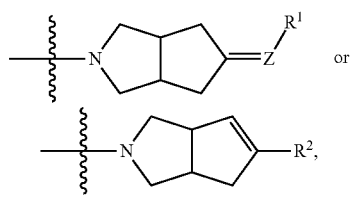

Z is nitrogen or carbon,
when the Z is nitrogen, R$^1$ is cyano group (—CN), and when the Z is carbon, R$^1$ is hydroxyl group (—OH), C$_1$-C$_7$ alkyloxy group, benzyloxy group, or cyano group (—CN), and
R$^2$ is cyano group or cyanomethyl group; and
when the X is 1H-1,2,3-triazol-1-yl group, Y is

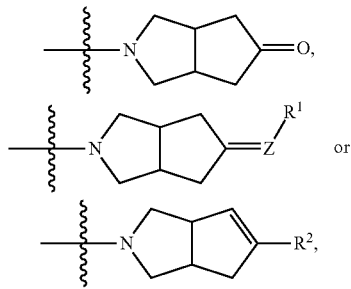

Z is nitrogen or carbon,
R$^1$ is hydroxy group (—OH), C$_1$-C$_7$ alkyloxy group, benzyloxy group, cyano group (—CN), or C$_1$-C$_7$ alkyloxycarbonyl group, and
R$^2$ is cyano group or cyanomethyl group.

Another embodiment provides a method for preparing the oxazolidinone derivative represented by the Chemical Formula 1 or a pharmaceutically acceptable salt thereof.

Yet another embodiment provides a pharmaceutical composition comprising the oxazolidinone derivative or a pharmaceutically acceptable salt thereof as an active ingredient.

Yet another embodiment provides an antibacterial composition comprising the oxazolidinone derivative or a pharmaceutically acceptable salt thereof as an active ingredient.

Yet another embodiment provides a method for controlling bacteria comprising applying the oxazolidinone derivative or a pharmaceutically acceptable salt thereof to a subject of bacteria control Yet another embodiment provides a method for preventing and/or treating an infectious disease caused by a pathogen, comprising administering a therapeutically effective amount of the oxazolidinone derivative represented by the Chemical Formula 1 or a pharmaceutically acceptable salt thereof to a patient in need thereof.

The pathogen may be at least one bacteria selected from the group consisting of *Staphylococcus* sp. bacteria, *Enterococcus* sp., *Escherichia coli, Bacillus* sp., *Salmonella* sp., and *Mycobacterium* sp. And, the pathogen may be a strain showing resistance to the existing antibiotics, for example, a methicillin-resistant strain, or a vancomycin-resistant strain.

Preferably, the method may further comprise identifying a patient in need of the prevention and/or treatment of an infectious disease caused by the pathogen, before the administration.

Hereinafter, the present invention will be explained in detail.

According to one embodiment of the invention, an oxazolidinone derivative represented by the Chemical Formula 1, or a pharmaceutically acceptable salt thereof is provided.

The oxazolidinone derivative represented by the Chemical Formula 1 includes a prodrug, hydrate, solvate and isomer thereof, as well as a pharmaceutically acceptable salt thereof.

The pharmaceutically acceptable salt is not specifically limited, it may be formed by reacting the oxazolidinone derivative represented by the Chemical Formula 1 with organic or inorganic acid, and for example, it may include hydrochloride, hydrobromide, methanesulfonate, hydroxyethansulfonate, sulfate, acetate, trifluoroacetate, maleate, benzenesulfonate, toluenesulfonate, nitrate, phosphate, borate, tartrate, citrate, succinate, benzoate, ascorbate, salicylate, and the like.

The oxazolidinone derivative represented by the Chemical Formula 1 may be preferably selected from the group consisting of compounds of the following Chemical Formula 2a, Chemical Formula 7a and Chemical Formulae 8 to 10.

[Chemical Formula 2a]

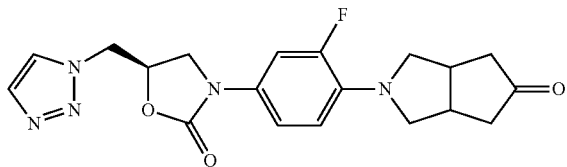

[Chemical Formula 7a]

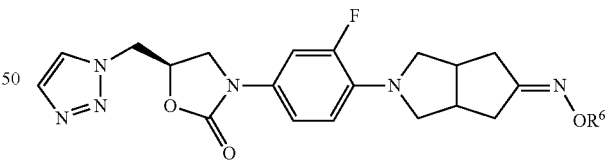

Wherein, R$^6$ is hydrogen, C$_1$-C$_7$ alkyl group, or benzyl group.

[Chemical Formula 8]

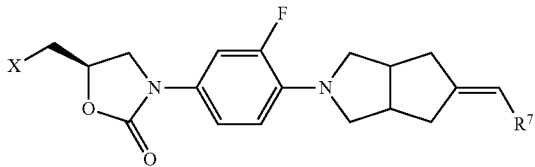

-continued

[Chemical Formula 9]

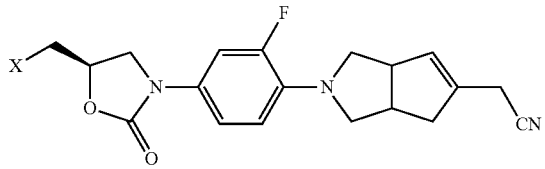

[Chemical Formula 10]

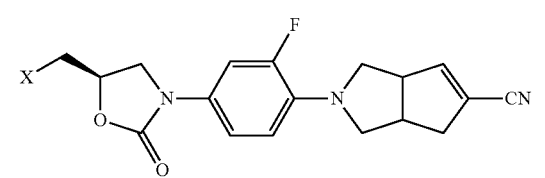

Wherein, Chemical Formulae 8 to 10,
X is acetamido (-NHAc) group or 1H-1,2,3-triazol-1-yl group,
R' is cyano group, or $C_1$-$C_7$ alkyloxycarbonyl group.

And, the oxazolidinone derivative represented by the Chemical Formula 1 may be preferably selected from the group consisting of compounds of the following 1) to 9).

1) N-[[(5S)-3-[4-(5-cyanomethylene-hexahydro-cyclopenta[c]pyrrol-2-yl)-3-fluorophenyl]-2-oxo-5-oxazolidinyl]methyl]acetamide
2) N-[[(5S)-3-[4-(5-cyanomethyl-3,3a,4,6a-tetrahydro-1H-cyclopenta[c]pyrrol-2-yl)-3-fluorophenyl]-2-oxo-5-oxazolidinyl]methyl]acetamide
3) N-[[(5S)-3-[4-(5-cyano-3,3a,4,6a-tetrahydro-1H-cyclopenta[c]pyrrol-2-yl)-3-fluorophenyl]-2-oxo-5-oxazolidinyl]methyl]acetamide
4) (5R)-3-[3-fluoro-4-(5-oxo-hexahydro-cyclopenta[c]pyrrol-2-yl)phenyl]-5-(1,2,3-triazol-1-ylmethyl)oxazolidin-2-one
5) (5R)-3-[3-fluoro-4-(5-hydroxyimino-hexahydro-cyclopenta[c]pyrrol-2-yl)phenyl]-5-(1,2,3-triazol-1-ylmethyl)oxazolidin-2-one
6) (5R)-3-[3-fluoro-4-(5-methoxyimino-hexahydro-cyclopenta[c]pyrrol-2-yl)phenyl]-5-(1,2,3-triazol-1-ylmethyl)oxazolidin-2-one
7) (5R)-3-[4-(5-cyanomethylene-hexahydro-cyclopenta[c]pyrrol-2-yl)-3-fluorophenyl]-5-(1,2,3-triazol-1-ylmethyl)oxazolidin-2-one
8) (5R)-3-[4-(5-cyanomethyl-3,3a,4,6a-tetrahydro-1H-cyclopenta[c]pyrrol-2-yl)-3-fluorophenyl]-5-(1,2,3-triazol-1-ylmethyl)oxazolidin-2-one
9) (5R)-3-[4-(5-cyano-3,3a,4,6a-tetrahydro-1H-cyclopenta[c]pyrrol-2-yl)-3-fluorophenyl]-5-(1,2,3-triazol-1-ylmethyl)oxazolidin-2-one It was confirmed that the oxazolidinone derivative of the Chemical Formula 1 or a pharmaceutically acceptable salt thereof exhibits approximately 2 times superior antibacterial activity against MRSA and other gram positive bacteria, compared to the existing oxazolidinone compound of linezolid (Upjohn).

Therefore, according to another embodiment of the invention, an antibacterial composition containing the oxazolidinone derivative or a pharmaceutically acceptable salt thereof as an active ingredient is provided.

The antibacterial composition may be used as a pharmaceutical composition for treating infectious diseases caused by the pathogen or antibiotics, as well as an antibacterial agent.

It was confirmed that the antibacterial composition exhibits excellent physiological activity against strains having resistance to the existing antibiotics, for example, methicillin-resistant strain or vancomycin-resistant strain. Particularly, it exhibits remarkably improved antibacterial activity against gram positive bacteria including various resistant strains, such as exhibiting high antibacterial activity against vancomycin resistant tuberculosis strain, which is a kind of super bacteria.

For example, the composition has an antibacterial activity against Staphylococcus sp., Enterococcus sp., Escherichia coli, Bacillus sp., Salmonella sp., and Mycobacterium sp., and the like, but not limited thereto.

The content of the oxazolidinone derivative of the Chemical Formula 1 or a pharmaceutically acceptable salt thereof, which is the active ingredient of the antibacterial composition, may be appropriately controlled according to the effect to be obtained, kind of bacteria, degree of infection, condition of a patient or a subject, and the like. For example, it may be included in the content of 0.0001 to 99.9 wt %, preferably 0.001 to 50 wt %, based on total weight of the composition.

Further, the antibacterial composition may be in the form of a pharmaceutical composition administered to vertebrate, preferably mammals or birds, or in the form of skin or hair wash, dish wash, clothes washing detergent, detergents for various stuffs, a common antibacterial agent, and the like, but not limited thereto.

If the composition is used in the form of a pharmaceutical composition, suitable carrier, excipient and diluent commonly used in the preparation of a pharmaceutical composition may be further included, and it may be formulated as an oral dosage form such as powder, granule, a tablet, a capsule, suspension, emulsion, syrup, aerosol, and the like, an external preparation, a suppository or a sterile injection solution, and the like.

The composition may be formulated using commonly used diluents or excipients such as a filler, a bulking agent, a binder, a wetting agent, a disintegrating agent, surfactant, and the like. A solid preparation for oral administration may include a tablet, pellet, powder, granule, a capsule, and the like, and the solid preparation may include at least one excipient and/or lubricant, and the like. A liquid preparation for oral administration may include suspension, oral liquid preparations, oil, syrup, and the like, and it may include various excipients, for example, a wetting agent, a sweetener, a flavoring agent, a preservative, and the like, in addition to commonly used simple diluent such as water, liquid paraffin. A preparation for parenteral administration may include a sterilized aqueous solution, a non-aqueous solvent, suspension, oil, a freeze dried preparation, a suppository, and the like.

Preferable dosage of the composition may be determined according to the kind of infected bacteria, degree of infection, body weight of a patient, form of drug, administration route and period, and the like. For obtaining preferable effects, the composition may be administered at a daily dosage of 0.01 mg/kg to 100 mg/kg, preferably 0.5 to 50 mg/kg, based on weight of the active ingredient for an adult patient with a body weight of 70 kg. It may be administered once a day or it may be dividedly administered several times a day.

The composition may be administered to animals, preferably mammals including human by various routes. For example, it may be administered by oral, intravenous, intramuscular or subcutaneous injection, and the like, and all the other possible administration routes may be applied. The pharmaceutical dosage form of the composition may be a pharmaceutically acceptable salt of an active ingredient, and it may be administered alone or in combination with other pharmaceutically active compounds.

According to yet another embodiment of the invention, a method for preparing an oxazolidinone derivative represented by the Chemical Formula 1 or a pharmaceutically acceptable salt thereof is provided.

[Chemical Formula 1]

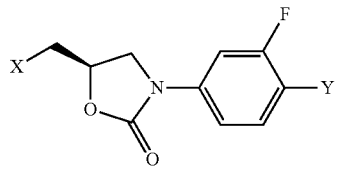

wherein,

X is acetamido (-NHAc) group or 1H-1,2,3-triazol-1-yl group,

Y is

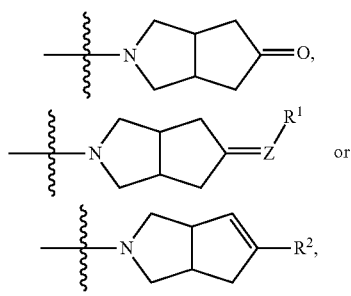

Z is nitrogen or carbon, $R^1$ is hydroxyl group (—OH), $C_1$-$C_7$ alkyloxy group, benzyloxy group, cyano group (—CN), or $C_1$-$C_7$ alkyloxycarbonyl group, and $R^2$ is cyano group or cyanomethyl group.

Preferably, when the X is acetamido (-NHAc) group, Y is

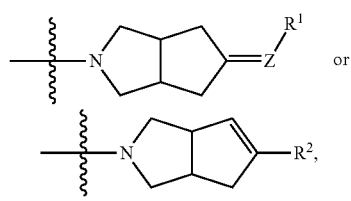

Z is nitrogen or carbon, when the Z is nitrogen, $R^1$ is cyano group (—CN), and when the Z is carbon, $R^1$ is hydroxyl group (—OH), $C_1$-$C_7$ alkyloxy group, benzyloxy group, or cyano group (—CN), and $R^2$ is cyano group or cyanomethyl group; and when the X is 1H-1,2,3-triazol-1-yl group, Y is

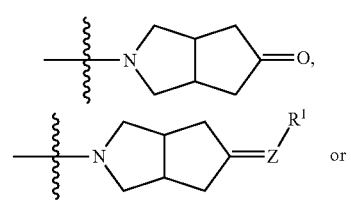

Z is nitrogen or carbon, $R^1$ is hydroxyl group (—OH), $C_1$-$C_7$ alkyloxy group, benzyloxy group, cyano group (—CN), or $C_1$-$C_7$ alkyloxycarbonyl group, and $R^2$ is cyano group or cyanomethyl group.

A compound of the Chemical Formula 1 wherein X is acetamido (-NHAc) group or 1H-1,2,3-triazol-1-yl group, and Y is

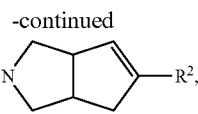

may be represented by the following Chemical Formula 2, and the compound of the Chemical Formula 2, although not limited, may be preferably prepared using a compound of the Chemical Formula A as a starting material and passing the compound of the Chemical Formula D as an intermediate, as shown in the following Reaction Equation 1-1.

[Chemical Formula 2]

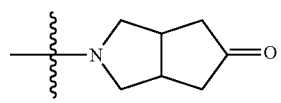

In the Chemical Formula 2, X is acetamido (-NHAc) group or 1H-1,2,3-triazol-1-yl group.

[Reaction Equation 1-1]

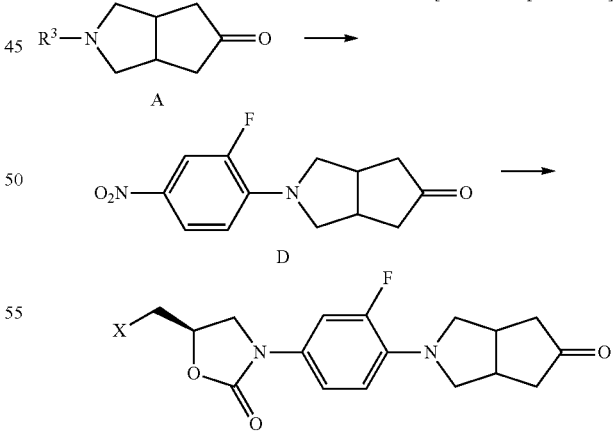

Chemical Formula 2

In the reaction equation 1-1, $R^3$ is $C_1$-$C_7$ alkyloxycarbonyl group or benzyl group, preferably tert-butoxycarbonyl, ethyloxycarbonyl, benzyloxycarbonyl or benzyl group.

The reaction equation 1-1 may be represented by the following reaction equation 1-2 in detail.

[Reaction Equation 1-2]
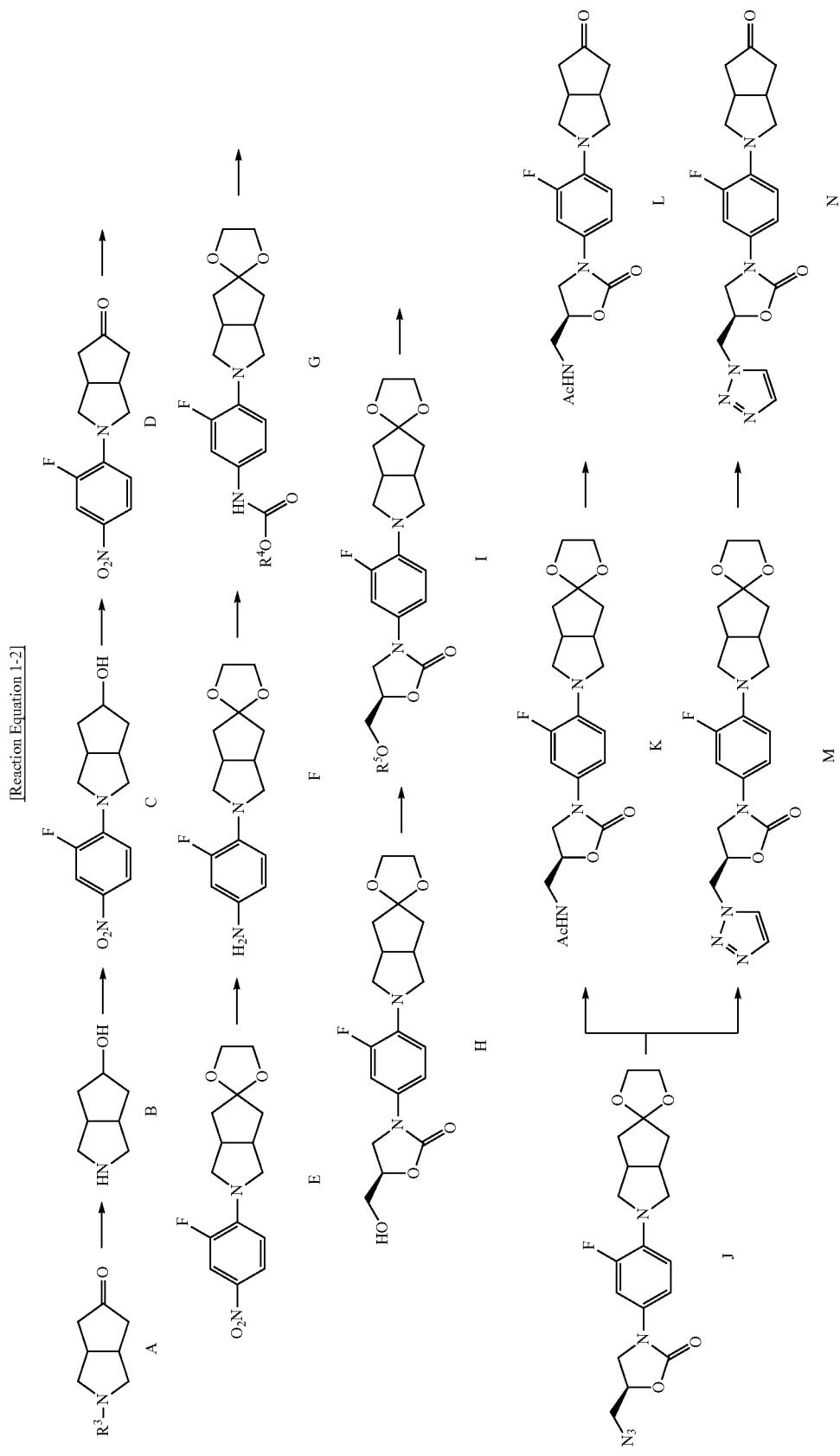

In the Reaction Equation 1-2, R³ is tert-butoxycarbonyl, ethyloxycarbonyl, benzyloxycarbonyl or benzyl group, R⁴ is methyl, ethyl or benzyl group, and R⁵ is methanesulfonyl group or p-toluenesulfonyl group.

In the step 1 (A→B) of the Reaction Equation 1-2, the compound A is dissolved in an organic solvent such as methanol, and the like, and cooled, sodium borohydride is added, acid such as concentrated hydrochloric acid or trifluoroacetic acid, and the like is added, and the mixture is stirred, and then, the solvent is removed to obtain the compound B.

The step 2 (B→C) is a nucleophilic aromatic substitution with 1,2-difluoro-4-nitrobenzene, wherein the compound B is dissolved in a solvent such as acetonitrile, tetrahydrofuran, ethyl acetate, dimethylsulfoxide, or dimethylformamide, and the like, 1,2-difluoro-4-nitrobenzne and appropriate base are added and heated to reflux to react them, thereby obtaining the compound C. The appropriate base may include N,N-diisopropylethylamine, triethylamine, pyridine, and the like, but not limited thereto. And, preferably, the reaction may be conducted at room temperature to 150° C.

The step 3 (C→D), although not limited, may be conducted under the PCC (pyridium chlorochromate), PDC (pyridium dichromate) or Swern oxidation condition, thereby obtaining the compound D.

The step 4 (D→E) is a ketal protection reaction of ketone, wherein the compound D and ethyleneglycol reagent are dissolved in a solvent such as benzene or toluene, and the like, and heated to reflux to obtain the compound E. As a catalyst, p-toluene sulfonic acid may be used, and the reaction may preferably be conducted at a temperature range of 80-120° C.

The step 5 (E→F) is a reduction of a nitro group, wherein the compound E is reacted under hydrogen using palladium/active carbon or Lindler catalyst or using tin dichloride under ethyl acetate, tetrahydrofuran, methanol, ethanol, methylene chloride, chloroform, or a mixed solvent thereof, thereby obtaining the compound F.

The step 6 (F→G) is a step wherein an aniline derivative (compound F) is dissolved in a solvent, base is added, and the mixture is cooled and then, reacted with benzyl chloroformate or methyl chloroformate to convert into a benzyl or methyl urethane derivative (compound G). As the solvent, tetrahydrofuran, a mixed solvent of water and acetone (9:1 to 10:1), or acetone may be preferably used, and as the base, triethylamine, sodium carbonate or sodium hydrogen carbonate, and the like may be used, but not limited thereto.

The step 7 (G→H) is preparation step of an oxazolidinone ring, wherein activation of urethane group is first required. Specifically, the compound G is dissolved in a tetrahydrofuran or dimethylformamide solvent and cooled, and then, base such as n-butyllithium, lithium diisopropylamide or lithium bis(trimethylsilyl)amide, and the like is slowly added to react them. The reaction may be preferably conducted at a temperature range of from −78° C. to −40° C., and if urethane group is activated, (−)-(R)-glycidyl butyrate is added and reacted at room temperature to obtain the compound H.

The step 8 (H→I) is a step wherein the hydroxyl group of the compound H is converted into methanesulfonate or p-toluenesulfonate, and methanesulfonyl chloride/pyridine, methanesulfonyl chloride/triethylamine/methylene chloride, methanesulfonyl chloride/triethylamine/dimethylsulfoxide or p-toluenesulfonyl chloride/pyridine, p-toluenesulfonyl chloride/triethylamine/methylene chloride may be used to obtain the compound I.

In the step 9 (I→J), the compound I and sodium azide or potassium azide are dissolved in a dimethylformamide or 1-methyl-2-pyrrolidinone solvent and reacted to obtain the compound J.

The step 10 may be divided into 2 steps.

One step is for introduction of an acetamide group (10-1 step: J→K)), wherein the compound J is dissolved in ethyl acetate, methanol, methylene chloride, chloroform, or a mixed solvent thereof, and acetic anhydride, and pyridine are added together with a catalyst of palladium, platinum or Lindler under hydrogen to acetylate, thereby obtaining the compound K including acetamide introduced therein.

The other step is for introduction of 1,2,3-triazol (10-2 step: J→M), wherein the compound J is dissolved in vinyl acetate, which is a solvent and simultaneously a reactant, and heated to reflux to obtain the compound M including 1,2,3-triazol introduced therein. Preferably, the reaction may be conducted at a temperature range of from 50° C. to 80° C.

The step 11 (K→L/M→N) is step of deprotecting the ketal group of the 10$^{th}$ product (compound K or compound M) to prepare a ketone compound L or N, wherein the compound K or compound M is dissolved in a mixed solvent of acetone and water, acid such as p-toluenesulfonic acid, hydrochloric acid or sulfuric acid, and the like is added and heated to reflux to react them, thereby obtaining the compound L or N.

A compound of the Chemical Formula 1 except a compound represented by the Chemical Formula 2, wherein X is an acetamido (-NHAc) group or a 1H-1,2,3-triazol-1-yl group, Y is

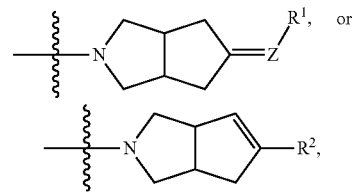

Z is nitrogen or carbon, R¹ is a hydroxyl group, a C₁-C₇ alkyloxy group, a benzyloxy group, a cyano group, or a C₁-C₇ alkyloxycarbonyl group, and R² is a cyano group or a cyanomethyl group, may be prepared by a method comprising converting a ketone group included in the bicyclic ring of the compound represented by the Chemical Formula 2.

The conversion of the ketone group of the compound represented by the Chemical Formula 2, although not limited, may be achieved by introducing at least one substituent selected from the group consisting of an oxyimino group, a methylene group, a cyanomethyl group, a C₁-C₇ alkyloxycarbonyl group and a cyano group in the ketone group included in the bicyclic ring of the compound represented by the Chemical Formula 2. And, preferably, the introduction of the substituent may be achieved by reacting the compound of the Chemical Formula 2 with one of the compounds of the following Chemical Formulae 3 to 6.

[Chemical Formula 3]

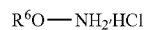

[Chemical Formula 4]

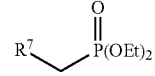

[Chemical Formula 5]

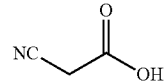

[Chemical Formula 6]

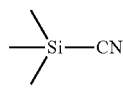

In the Chemical Formula 3, $R^6$ is hydrogen, $C_1$-$C_7$ alkyl group or benzyl group, and in the Chemical Formula 4, $R^7$ is cyano group or $C_1$-$C_7$ alkyloxycarbonyl group.

For example, when Z is nitrogen, and $R^1$ is hydroxyl group (—OH), $C_1$-$C_7$ alkyloxy group, or benzyloxy group, a compound of the Chemical Formula 1 may be represented by the following Chemical Formula 7, which may be prepared by introducing an oxyimino group in the ketone group of the compound of the Chemical Formula 2.

[Chemical Formula 7]

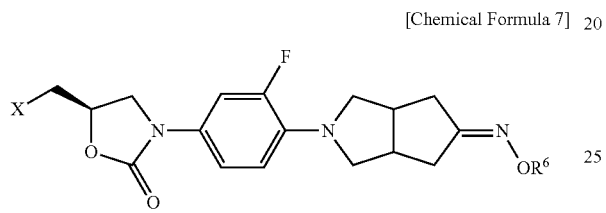

In the Chemical Formula 7,
X is as defined in the Chemical Formula 1, and
$R^6$ is hydrogen, $C_1$-$C_7$ alkyl group, or benzyl group.

The introduction of the oxyimino group may be conducted by condensation reaction of the compound of the Chemical Formula 2 and the compound of the Chemical Formula 3, which is represented by the following Reaction Equation 2, but is not limited thereto.

[Reaction Equation 2]

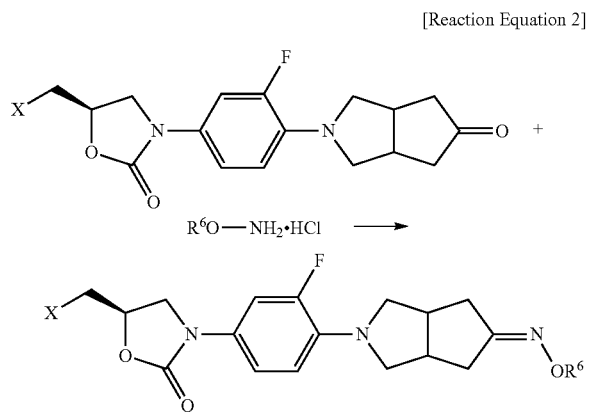

In the reaction equation 2, X is as defined in the Chemical Formula 1, and $R^6$ may be preferably hydrogen, $C_1$-$C_7$ alkyl group or benzyl group.

Specifically, the compound of the Chemical Formula 2 is dissolved in a mixed solvent of alcohol and water or water, and based such as sodium carbonate, sodium hydrogen carbonate, sodium hydroxide or potassium hydroxide, and the like, and the compound of the Chemical Formula 3 are added to react them, thereby introducing an oxyimino group in the ketone group of the compound of the Chemical Formula 2. The reaction may be preferably conducted at room temperature.

And when Z is carbon, and $R^1$ is cyano group or $C_1$-$C_7$ alkyloxycarbonyl group, a compound of the Chemical Formula 1 may be represented by the following Chemical Formula 8, which may be prepared by introducing a methylene group in the ketone group of the compound of the Chemical Formula 2.

[Chemical Formula 8]

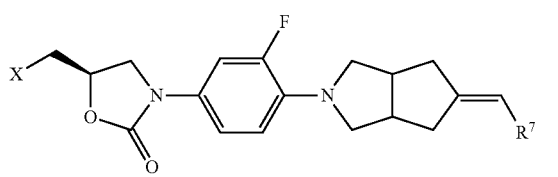

In the Chemical Formula 8,
X is as defined in the Chemical Formula 1, and
$R^7$ is cyano group, or $C_1$-$C_7$ alkyloxycarbonyl group.

The introduction of the methylene group may be conducted by Wadsworth-Horner-Emmons reaction of the compound of the Chemical Formula 2 with a compound of the Chemical Formula 4, which may be represented by the following Reaction Equation 3.

[Reaction Equation 3]

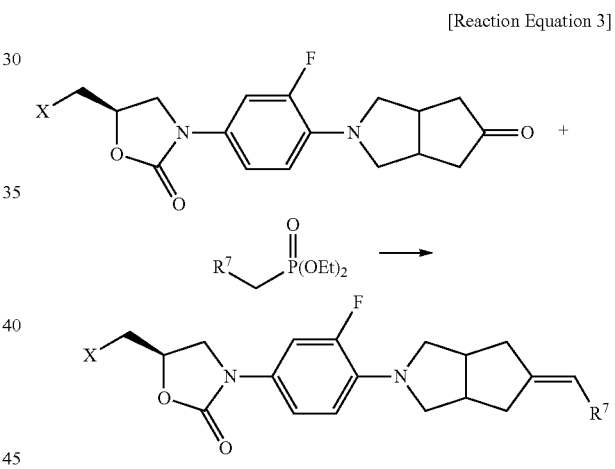

In the Reaction Equation 3, X and $R^7$ are as defined in the Chemical Formula 1, preferably $R^7$ is cyano group or $C_1$-$C_7$ alkyloxycarbonyl group.

In the Reaction Equation 3, activation of the phosphonate group is first required. Base suitable for the activation of the phosphonate group may include sodium hydride, n-butyllithium, potassium t-butoxide, and the like, but is not limited thereto. The activation may be achieved by dissolving the base in a solvent such as purified tetrahydrofuran, didiethyl ether or dimethoxyethane, and the like, and cooling, and then, adding the compound of the Chemical Formula 4. The temperature for the activation of phosphonate may be preferably 0° C. to room temperature. To the activated phosphonate solution, the compound of the Chemical Formula 2 is added and stirred. The mixture may be heated to reflux at a temperature of room temperature or 40-100° C.

And when $R^2$ is cyanomethyl group, a compound of the Chemical Formula 1 may be represented by the following Chemical Formula 9, which may be prepared by introducing cyanomethyl group in the ketone group of the compound of the Chemical Formula 2.

[Chemical Formula 9]

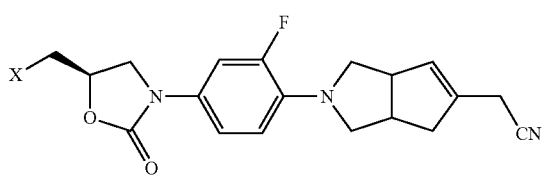

In the Chemical Formula 9, X is as defined in the Chemical Formula 1.

The introduction of the cyanomethyl group may be conducted by Knoevenagel reaction of the compound of the Chemical Formula 2 and the compound of the Chemical Formula 5 and decarboxylation, which may be represented by the following Reaction Equation 4.

[Reaction Equation 4]

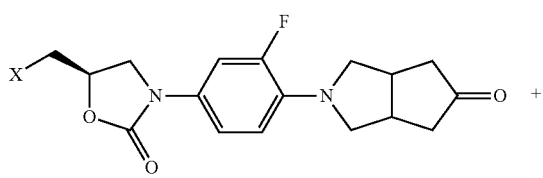

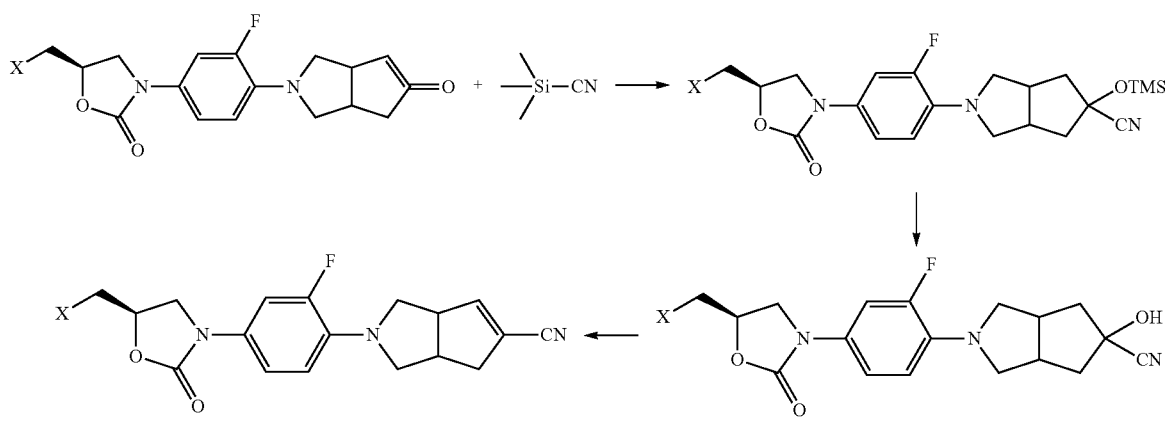

In the Reaction Equation 4, X is as defined in the Chemical Formula 1.

The Reaction Equation 4 may be conducted by dissolving a compound of the Chemical Formula 2 in a methylene chloride or benzene solvent with a catalyst such as ammonia, ammonia salt, triethylamine, piperidine, potassium fluoride, cerium fluoride, titanium chloride or aluminum oxide, and the like, or reacting it with a compound of the Chemical Formula 5 at room temperature or 50-100° C. without a solvent.

And when $R^2$ is cyano group, a compound of the Chemical Formula 1 may be represented by the following Chemical Formula 10, which may be prepared by introducing cyano group in the ketone group of the compound of the Chemical Formula 2.

[Chemical Formula 10]

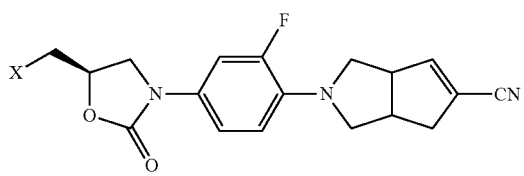

In the Chemical Formula 10, X is as defined in the Chemical Formula 1.

The introduction of the cyano group may be conducted by cyanosilylation of the compound of the Chemical Formula 2 with a compound of the Chemical Formula 6 and dehydration, which may be represented by the following Reaction Equation 5.

[Reaction Equation 5]

In the Reaction Equation 5, X is as defined in the Chemical Formula 1.

Specifically, in step 1 of the Reaction Equation 5, the compound of the Chemical Formula 2 is dissolved in a solvent such as methylene chloride, benzene, toluene, didiethyl ether, acetonitrile, and the like together with a catalyst such as indium bromide, aluminum chloride, tin chloride, zinc chloride, titanium chloride, and the like, and cooled, and then, a compound of the Chemical Formula 6 is added dropwise to conduct cyanosilylation.

In the step 2 of the Reaction Equation 5, a TMS group bonded in the oxygen may be simply removed using formic acid.

In the final 3 step, pyridine is used as a solvent, and phosphorous oxychloride is added and stirred to complete introduction of cyano group in the ketone group of the compound of the Chemical Formula 2.

Meanwhile, all the steps of the reaction may be preferably conducted at room temperature.

As explained above, to prepare the compound of the Chemical Formula 1, conversion of the ketone group included in the bicyclic ring of the compound of the Chemical Formula 2 may be conducted according to the Reaction Equations 2 to 5. And, the prepared novel oxazolidinone derivative of the Chemical Formula 1 and a pharmaceutically acceptable salt thereof exhibit remarkably improved antibacterial activity against strains showing resistance to the existing antibiotics, and an antibacterial composition comprising the same may be used as various pharmaceutical compositions for preventing and/or treating infectious diseases caused by the pathogen or antibiotics, as well as an antibacterial agent.

Yet another embodiment provides a bacteria controlling method comprising applying the oxazolidinone derivative or a pharmaceutically acceptable salt thereof to a subject of bacteria control. The subject may be various stuffs and animals, for example, mammals including human or birds, and the application may be conducted by spraying or coating the oxazolidinone derivative or a pharmaceutically acceptable salt thereof on the stuff or administering it to the animals.

The oxazolidinone derivative or a pharmaceutically acceptable salt thereof may be formulated as a drug, skin or hair wash, dish wash, clothes washing detergent, detergents for various stuffs, common antibacterial agent, and the like, but not limited thereto.

According to yet another embodiment of the invention, a method for treating and/or preventing an infectious disease caused by a pathogen, comprising administering a therapeutically effective amount of the oxazolidinone derivative or a pharmaceutically acceptable salt thereof to a patient in need thereof.

The pathogen may be at least one selected from the group consisting of *Staphylococcus* sp. bacteria, *Enterococcus* sp., *Escherichia coli*, *Bacillus* sp., *Salmonella* sp., and *Mycobacterium* sp. And, the pathogen may be a strain having resistance to the existing antibiotics, for example, methicillin-resistant strain or vancomycin-resistant strain.

Preferably, the oxazolidinone derivative or a pharmaceutically acceptable salt thereof may be administered together with a pharmaceutically acceptable carrier, excipient and diluent, which may be the same as explained in the antibacterial composition of the present invention.

The therapeutically effective amount may be preferably 0.01 mg/kg/day to 100 mg/kg/day, more preferably 0.5 to 50 mg/kg/day, but is not limited thereto. It may be administered once a day or dividedly administered several times a day.

Preferably, the method may further include identifying a patient requiring prevention and/or treatment of infectious disease caused by pathogen before the administration.

The patient may be an animal, preferably mammals including human, and it may be administered by oral, intravenous, intramuscular, or subcutaneous injection, and the like, but not limited thereto.

According to the present invention, an oxazolidinone derivative including a novel bicyclic ring or a pharmaceutically acceptable salt thereof, and a preparation method thereof are provided. The compound has excellent physiological activity against strains having resistance to the existing antibiotics, exhibits excellent efficacy against gram positive bacteria including various resistant strains, particularly exhibiting high antibacterial activity against vancomycin-resistant tuberculosis strain, which is a kind of super bacteria, and has very excellent effects in terms of toxicity and stability. Therefore, it may be useful for an antibacterial agent, antibiotics, or a pharmaceutical composition for treating infectious disease caused by pathogen.

Hereinafter, the present invention will be explained in more detail with reference to the following examples. However, these examples are only to illustrate the invention and the scope of the invention is not limited thereto.

Preparation Example 1

Preparation of N-[[(5S)-3-[3-fluoro-4-(5-oxo-hexahydro-cyclopenta[c]pyrrol-2-yl)phenyl]-2-oxo-5-oxazolidinyl]methyl]acetamide and hydrochloride thereof Step 1

Preparation of octahydro-5-hydroxycyclopenta[c]pyrrol hydrochloride 10.00 g (44.4 mmol) of 5-oxo-hexahydro-cyclopenta[c]pyrrol-2-carboxylic acid tert-butyl ester (Hanchem Co. Ltd.) was dissolved in 100 ml of methanol, the temperature was lowered to 0° C., 3.36 g (88.8 mmol) of sodium borohydride was added, and then, the mixture was stirred for 1 hour. And, 15 ml of an aqueous solution of concentrated hydrochloric acid (35% (v/v)) was slowly added, and the mixture was additionally stirred for 1 hour, and then, the solvent was removed under reduced pressure to obtain the title compound.

Step 2

Preparation of 2-(2-fluoro-4-nitrophenyl)-octahydro-5-hydroxycyclopenta[c]pyrrol The octahydro-5-hydroxycyclopenta[c]pyrrol hydrochloride (44.4 mmol) prepared in the step 1 was dissolved in 100 ml of acetonitrile, and 4.91 ml (44.4 mmol) of 1,2-difluoro-4-nitrobenzene and 23.20 ml (133.2 mmol) of N,N-diisopropylethylamine were added, and the mixture was heat to reflux for 6 hours. After the reaction was completed, the temperature was lowered to room temperature, and the mixture was concentrated under reduced pressure to remove the solvent. The solvent-free concentrate was dissolved in ethyl acetate, and washed with distilled water, and then, the organic layer was dried over magnesium sulfate, filtered and concentrated under reduced pressure to obtain the title compound, of which NMR data is as follow.

$^1$H NMR (CDCl$_3$, 300 MHz) δ 7.88 (m, 2H), 6.66 (t, J=8.7 Hz, 1H), 4.34 (t, J=4.8 Hz, 1H), 3.60 (m, 4H), 2.82 (m, 2H), 2.21 (m, 2H), 1.70 (t, J=4.5 Hz, 1H), 1.65 (t, J=3.9 Hz, 1H)

$^{13}$C NMR (CDCl$_3$, 75 MHz) δ 152.03, 148.77, 142.78, 142.66, 121.46, 115.25, 115.17, 112.73, 112.38, 74.34, 57.21, 41.99, 41.77, 40.81, 40.68

Step 3

Preparation of 2-(2-fluoro-4-nitrophenyl)-5-oxo-hexahydro-cyclopenta[c]pyrrol 5.8 ml (66.6 mmol) of oxalyl chloride (COCl$_2$) was dissolved in 100 ml of methylene chloride, and the solution was cooled to −78° C., and then, 9.45 ml (133.2 mmol) of dimethyl sulfoxide was slowly added dropwise for 30 minutes, and the mixture was stirred for 30 minutes.

And, then, the 2-(2-fluoro-4-nitrophenyl)-octahydro-5-hydroxycyclopenta[c]pyrrol (44.4 mmol) prepared in the step 2 was dissolved in 100 ml of methylene chloride and slowly added over 30 minutes, the mixture was stirred for 1 hour while maintaining the temperature, and then, 30.93 ml (221.9 mmol) of triethylamine was slowly added over 20 minutes, the temperature was raised to room temperature, and the mixture was stirred for 2 hours. After the reaction was completed, 100 mL of methylene chloride was added to dilute the mixture, and then, the mixture was washed with water and a saturated aqueous solution of sodium chloride, and the organic layer was dried over magnesium sulfate, filtered and concentrated under reduced pressure. The concentrate was recrystallized under ethanol solvent to obtain 11.1 g (95%) of the title compound.

Step 4

Preparation of 2-(2-fluoro-4-nitrophenyl)-hexahydro-1H-spiro[cyclopenta[c]pyrrol-5,2'-[1,3]dioxolane]

19.74 g (74.7 mmol) of 2-(2-fluoro-4-nitrophenyl)-5-oxo-hexahydro-cyclopenta[c]pyrrol prepared in the step 3 and 5.0 ml (89.6 mmol) of ethylene glycol were dissolved in 200 ml of benzene, 1.00 g (5.2 mmol) of p-toluene sulfonic acid hydrate was added, and the mixture was heated to reflux for 1 hour while removing generated water. After the reaction was completed, the mixture was washed with a saturated aqueous solution of sodium carbonate and water, and then, the organic layer was dried over magnesium sulfate, filtered and concentrated under reduced pressure to obtain the title compound, of which NMR data is as follow.

$^1$H NMR (CDCl$_3$, 300 MHz) δ 7.88 (m, 2H), 6.57 (t, J=8.9 Hz, 1H), 3.92 (m, 4H), 3.74 (m, 2H), 3.52 (t, J=4.5 Hz, 1H), 3.48 (t, J=3.2 Hz, 1H), 2.86 (m, 1H), 2.17 (dd, J=13.9, 8.7 Hz, 2H), 1.84 (dd, J=13.9, 5.8 Hz, 2H)

$^{13}$C NMR (CDCl$_3$, 75 MHz) δ 151.11, 147.86, 142.55, 142.43, 136.87, 136.76, 121.66, 114.10, 114.03, 113.46, 113.39, 112.91, 112.56, 112.44, 112.16, 455.70, 55.62, 54.93, 54.85, 50.09, 48.82, 42.40, 39.82, 39.80, 39.30, 38.88, 38.85

Step 5

Preparation of 2-(4-amino-2-fluorophenyl)-hexahydro-1H-Spiro[cyclopenta[c]pyrrol-5,2'-[1,3]dioxolane]

2-(2-fluoro-4-nitrophenyl)-hexahydro-1H-spiro[cyclopenta pyrrol-5,2'-[1,3]dioxolane] (74.7 mmol) prepared in the step 4 was dissolved in 200 ml of ethyl acetate, 2 g of 10% palladium/active carbon was added, and the mixture was stirred for 10 hours under hydrogen balloon. After the reaction was completed, the mixture was filtered to remove solid, concentrated under reduced pressure to obtain the title compound, of which NMR data is as follows.

$^1$H NMR (CDCl$_3$, 300 MHz) δ 7.91 (m, 2H), 6.59 (t, J=8.9 Hz, 1H), 3.67 (m, 2H), 3.48 (m, 2H), 3.21 (s, 4H), 2.84 (m, 2H), 2.25 (dd, J=13.5, 8.3 Hz, 2H), 1.73 (dd, J=13.6, 6.3 Hz, 2H)

Step 6

Preparation of 2-[4-[[(benzyloxy)carbonyl]amino]-2-fluorophenyl]-hexahydro-1H-spiro[cyclopenta[c]pyrrol-5,2'-[1,3]dioxolane]

2-(4-amino-2-fluorophenyl)-hexahydro-1H-spiro[cyclopenta[c]pyrrol-5,2'-[1,3]dioxolane] (74.7 mmol) prepared in the step 5 was dissolved in 300 ml of acetone, and 150 ml of a 10 wt % sodium carbonate aqueous solution was added. And then, the temperature was lowered to 0° C., 13.86 ml (97.1 mmol) of benzyl chloroformate was slowly added dropwise over 30 minutes, and the mixture was stirred for 12 hours while raising the temperature to room temperature. After the reaction was completed, the solvent was removed under reduced pressure, 300 ml of ethyl acetate was added, the mixture was washed with water and sodium chloride, and then, the organic layer was dried over magnesium sulfate and filtered and concentrated under reduced pressure. The concentrate was separated by column chromatography to obtain 24.1 g (78%) of the title compound, of which NMR data is as follows.

$^1$H NMR (CDCl$_3$, 300 MHz) δ 7.28 (m, 5H), 6.91 (m, 1H), 6.63 (m 2H), 5.17 (s, 2H), 3.90 (m, 4H), 3.23 (m, 2H), 3.16 (m, 2H), 2.78 (m, 1H), 2.07 (dd, J=13.1, 7.9 Hz, 2H), 1.79 (dd, J=13.1, 5.9 Hz, 2H)

Step 7

Preparation of 2-[2-fluoro-4-[(5R)-5-(hydroxymethyl)-2-oxo-3-oxazolidinyl]phenyl]-hexahydro-1H-spiro[cyclopenta[c]pyrrol-5,2'-[1,3]dioxolane]

24.12 g (58.5 mmol) of 2-[4-[[(benzyloxy)carbonyl]amino]-2-fluorophenyl]-hexahydro-1H-spiro[cyclopenta[c]pyrrol-5,2'-[1,3]dioxolane] prepared in the step 6 was dissolved in 250 ml of tetrahydrofuran, the temperature was cooled to −78° C., and 44 ml (70.4 mmol) of 1.6 M n-butyllithium was slowly added over 30 minutes. After the reaction mixture was stirred for 1 hour, 9.11 ml (60.0 mmol) of (−)-(R)-glycidyl butyrate was added dropwise over 30 minutes, and the mixture was stirred for 12 hours while raising the temperature to room temperature. After the reaction was completed, the solvent was removed under reduced pressure, 250 ml of ethyl acetate was added, the mixture was washed with a saturated aqueous solution of ammonium chloride and distilled water, dried over magnesium sulfate, filtered, and concentrated under reduced pressure to obtain 21.4 g (97%) of the title compound, of which NMR data is as follows.

$^1$H NMR (CDCl$_3$, 300 MHz) δ 7.35 (m, 1H), 7.07 (m, 1H), 6.73 (t, J=9.2 Hz, 1H), 4.72 (m, 1H), 3.99 (part A of AB system, J=8.7 Hz, 1H), 3.94 (part B of AB system, J=8.7 Hz, 1H), 3.92 (s, 4H), 3.76 (m, 2H), 3.30 (m, 2H), 3.21 (m, 2H), 2.81 (m, 2H), 2.10 (dd, J=13.3, 8.3 Hz, 2H), 1.81 (dd, J=13.3, 3.4 Hz, 2H)

Step 8

Preparation of 2-[2-fluoro-4-[(5R)-5-[[(methylsulfonyl)oxy]methyl]-2-oxo-3-oxazolidinyl]phenyl]-hexahydro-1H-spiro[cyclopenta[c]pyrrol-5,2'-[1,3]dioxolane]

21.4 g (56.6 mmol) of 2-[2-fluoro-4-[(5R)-5-(hydroxymethyl)-2-oxo-3-oxazolidinyl]phenyl]-hexahydro-1H-spiro[cyclopenta[c]pyrrol-5,2'-[1,3]dioxolane] prepared in the step 7 was dissolved in 200 ml of methylene chloride, 19.7 ml (141.5 mmol) of triethylamine was added, the temperature was lowered to 0° C., and then, 8.76 ml (113.2 mmol) of methansulfonyl chloride was added dropwise over 15 minutes, and the mixture was stirred for 1 hour. After the reaction was completed, the reaction mixture was diluted with 200 mL of methylene chloride, washed with water and a saturated aqueous solution of sodium chloride, and then, dried over magnesium sulfate, filtered and concentrated under reduced pressure to obtain the title compound.

Step 9

Preparation of 2-[2-fluoro-4-[(5R)-5-(azidomethyl)-2-oxo-3-oxazolidinyl]phenyl]-hexahydro-1H-spiro[cyclopenta[c]pyrrol-5,2'-[1,3]dioxolane]

2-[2-fluoro-4-[(5R)-5-[[(methylslufonyl)oxy]methyl]-2-oxo-3-oxazolidinyl]phenyl]-hexahydro-1H-spiro[cyclopenta[c]pyrrol-5,2'-[1,3]dioxolane] (56.60 mmol) prepared in the step 8 and 29.44 g (452.8 mmol) of sodium azide were dissolved in 500 ml of dimethylformamide, and then, the mixture was stirred at 75° C. for 2 hours. After the reaction was completed, the temperature was lowered to room temperature, water was added, and the mixture was extracted with ethyl acetate. And then, the organic layer was dried over magnesium sulfate, filtered and concentrated under reduced pressure to obtain the title compound.

Step 10

Preparation of 2-[4-[(5S)-5-[(acetylamino)methyl]-2-oxo-3-oxazolidinyl]-2-fluoro phenyl]-hexahydro-1H-spiro[cyclopenta[c]pyrrol-5,2'-[1,3]dioxolane]

10 g (24.8 mmol) of 2-[2-fluoro-4-[(5R)-5-(azidomethyl)-2-oxo-3-oxazolidinyl]phenyl]-hexahydro-1H-spiro[cyclopenta[c]pyrrol-5,2'-[1,3]dioxolane] prepared in the step 9 was dissolved in 100 ml of ethyl acetate, and 1 g of 10% palladium/active carbon, 4.01 ml (45.6 mmol) of pyridine and 3.5 ml (37.2 mmol) of acetic anhydride were added, and then, the mixture was stirred for 5 hours under hydrogen gas balloon. After the reaction was completed, the reaction mixture was filtered to remove solid and concentrated under reduced pressure. The concentrate was separated by column chromatography to obtain 5.30 g (51%) of the title compound, of which NMR data is as follows.

$^1$H NMR (CDCl$_3$, 300 MHz) δ 7.31 (m, 1H), 6.98 (m, 1H), 6.79 (t, J=Hz, 1H), 4.75 (m, 1H), 3.98 (t, J=9.0 Hz, 1H), 3.88 (s, 4H), 3.72 (t, J=6.8 Hz, 1H), 3.61 (m, 2H), 3.27 (m, 2H), 3.22 (m, 2H), 2.78 (m, 2H), 2.08 (dd, J=13.2, 8.2 Hz, 2H), 1.78 (dd, J=13.2, 6.1 Hz, 2H)

Step 11

Preparation of N-[[(5S)-3-[3-fluoro-4-(5-oxo-hexahydro-cyclopenta[c]pyrrol-2-yl)phenyl]-2-oxo-5-oxazolidinyl]methyl]acetamide and hydrochloride thereof 2 g (4.77 mmol) of 2-[4-[(5S)-5-[(acetylamino)methyl]-2-oxo-3-oxazolidinyl]-2-fluorophenyl]-hexahydro-1H-spiro[cyclopenta[c]pyrrol-5,2'-[1,3]dioxolane] prepared in the step 10 was dissolved in 60 ml of, acetone, 20 ml of water was added, 1.81 g (9.53 mmol) of p-toluene sulfonic acid hydrate was added, and then, the mixture was heated to reflux for 6 hours. After the reaction was completed, a saturated aqueous solution of sodium hydrogen carbonate was added, and acetone was removed under reduced pressure. The aqueous solution layer was extracted with ethyl acetate, and the organic layer was dried over magnesium sulfate, filtered and concentrated under reduced pressure. The concentrate was separated by column chromatography to obtain 1.31 g (73%) of the title compound, of which NMR data is as follows.

$^1$H NMR (CDCl$_3$, 300 MHz) δ 8.37 (dd, J=15.3, 2.1 Hz, 1H), 7.05 (dd, J=8.7, 2.7 Hz, 1H), 6.69 (t, J=9.3 Hz, 1H), 6.24 (t, J=5.7 Hz, 1H), 4.77 (m, 1H), 4.03 (t, J=9.1 Hz, 1H), 3.68 (m, 5H), 3.30 (d, J=17.4 Hz, 2H), 3.07 (br s, 2H), 2.60 (dd, J=19.2, 8.1 Hz, 2H), 2.29 (dd, J=19.5, 3.3 Hz, 2H), 2.05 (s, 3H)

And, 400 mg of the compound obtained in the step 11 was dissolved in 5 mL of dichloromethane, treated with 10 mL of diethyl ether saturated with hydrogen chloride gas, and then, 40 mL of diethyl ether was added and the product was filtered to quantitatively obtain hydrochloride.

Example 1

Preparation of N-[[(5S)-3-[4-(5-cyanomethylene-hexahydro-cyclopenta[c]pyrrol-2-yl)-3-fluorophenyl]-2-oxo-5-oxazolidinyl]methyl]acetamide and hydrochloride thereof 30 mg (0.27 mmol) of potassium tert-butoxide was dissolved in 10 ml of tetrahydrofuran, and the temperature was lowered to −78° C. And then, 234 mg (0.33 mmol) of diethylcyanomethyl phosphonate was slowly added and the mixture was stirred for 1 hour.

And then, 100 mg (0.27 mmol) of N-[[(5S)-3-[3-fluoro-4-(5-oxo-hexahydro-cyclopenta[c]pyrrol-2-yl)phenyl]-2-oxo-5-oxazolidinyl]methyl]acetamide 100 mg (0.27 mmol) prepared in the preparation example 1 was dissolved in 10 ml of tetrahydrofuran and slowly added, and then, the mixture was stirred for 3 hours while slowly raising the temperature to room temperature. After the reaction was completed, the solvent was removed under reduced pressure, water was added to the mixture, and the mixture was extracted with methylene chloride. And then, the organic layer was dried over magnesium sulfate, filtered and concentrated under reduced pressure. The concentrate was separated by column chromatography using 2% (v/v) methanol-ethyl acetate to obtain 88 mg (83%) of the title compound, of which NMR data is as follows.

$^1$H NMR (CDCl$_3$, 300 MHz) δ 7.31 (dd, J=15.0, 2.4 Hz, 1H), 7.06 (t, J=6.0 Hz, 1H), 6.97 (dd, J=8.9, 2.3 Hz, 1H), 6.61 (t, J=9.0 Hz, 1H) 5.24 (t, J=2.0 Hz, 1H), 4.74 (m, 1H), 3.97 (t, J=9.0 Hz, 1H), 3.72 (dd, J=8.7, 6.6 Hz, 1H), 3.6 J=5.3 Hz, 2H), 3.45 (m, 1H), 3.43 (s, 1H), 3.14 (m, 2H), 2.90 (m, 3H), 2.78 (m, 1H), 2.56 (m, 1H), 2.46 (m, 1H), 2.00 (s, 3H)

$^{13}$C NMR (CDCl$_3$, 75 MHz) δ 172.62, 171.79, 155.01, 154.10, 150.89, 134.12, 133.98, 129.77, 129.63, 117.30, 116.36, 116.29, 114.83, 108.33, 107.99, 91.97, 72.23, 56.11, 56.05, 55.97, 48.12, 42.21, 42.14, 41.86, 39.77, 38.85, 23.19

And, the obtained compound was treated with diethyl ether saturated with hydrogen chloride gas by the same method as the step 11 of the preparation example to obtain hydrochloride thereof.

Example 2

Preparation of N-[[(5S)-3-[4-(5-cyanomethyl-3,3a,4,6a-tetrahydro-1H-cyclopenta[c]pyrrol-2-yl)-3-fluorophenyl]-2-oxo-5-oxazolidinyl]methyl]acetamide and hydrochloride thereof 100 mg (0.27 mmol) of N-[[(5S)-3-[3-fluoro-4-(5-oxo-hexahydro-cyclopenta[c]pyrrol-2-yl)phenyl]-2-oxo-5-oxazolidinyl]methyl]acetamide prepared in the preparation example 1 and 2 mg (0.03 mmol) of ammonium acetate were dissolved in 5 ml of benzene, 23 mg (0.27 mmol) of cyanoacetic acid was added, and the mixture was heated to reflux for 20 hours while removing water. After the reaction was completed, water was added and the mixture was extracted with methylene chloride, and then, the organic layer was dried over magnesium sulfate, filtered and concentrated under reduced pressure. The concentrate was separated by column chromatography using 2% (v/v) methanol-ethyl acetate to obtain 31 mg (30%) of the title compound, of which NMR data is as follows.

$^1$H NMR (CD$_3$OD, 300 MHz) δ 8.10 (d, J=1.2 Hz, 1H), 7.79 (d, J=1.2 Hz, 1H), 7.30 (dd, J=15.0, 2.4 Hz, 1H), 7.02 (dd, J=9.0, 2.7 Hz, 1H), 6.84 (t, J=9.0 Hz, 1H), 5.69 (d, J=2.4 Hz, 1H), 5.14 (m, 1H), 4.89 (m, 2H), 4.25 (t, J=9.3 Hz, 1H), 3.96 (dd, J=9.3, 5.4 Hz, 1H), 3.51-3.08 (m, 6H), 2.78 (dd, J=16.5, 8.1 Hz, 1H), 2.31 (dd, J=16.8, 1.5 Hz, 1H)

And, the obtained compound was treated with diethyl ether saturated with hydrogen chloride gas by the same method as the step 11 of the preparation example 1 to obtain hydrochloride thereof.

Example 3

Preparation of N-[[(5S)-3-[4-(5-cyano-3,3a,4,6a-tetrahydro-1H-cyclopenta[c]pyrrol-2-yl)-3-fluorophenyl]-2-oxo-5-oxazolidinyl]methyl]acetamide and hydrochloride Step 1

Preparation of N-[[(5S)-3-[4-(5-cyano-5-trimethylsilanyloxy-hexahydro-cyclopenta[c]pyrrol-2-yl)-3-fluorophenyl]-2-oxo-5-oxazolidinyl]methyl]acetamide 300 mg (0.80 mmol) of N-[[(5S)-3-[3-fluoro-4-(5-oxo-hexahydro-cyclopenta[c]pyrrol-2-yl)phenyl]-2-oxo-5-oxazolidinyl]methyl]acetamide prepared in the preparation example 1 and 30 mg (0.09 mmol) of indium tribromide were dissolved in 5 ml of methylene chloride and the temperature was lowered to 0° C., and then, 357 mg (3.60 mmol) of trimethylsilyl cyanide was slowly added and the mixture was stirred for 20 hours. After the reaction was completed, a saturated aqueous solution of sodium hydrogen carbonate was added and the mixture was extracted with methylene chloride, and then, the organic layer was dried over magnesium sulfate, filtered and concentrated under reduced pressure. The concentrate was separated by column chromatography using 2% (v/v) methanol-ethyl acetate to obtain 242 mg (64%) of N-[[(5S)-3-[4-(5-cyano-5-trimethylsilanyloxy-hexahydro-cyclopenta[c]pyrrol-2-yl)-3-fluorophenyl]-2-oxo-5-oxazolidinyl]methyl]acetamide.

<Step 2> Removal of TMS Group

To 140 mg (0.29 mmol) of N-[[(5S)-3-[4-(5-cyano-5-trimethylsilanyloxy-hexahydro-cyclopenta[c]pyrrol-2-yl)-3-fluorophenyl]-2-oxo-5-oxazolidinyl]methyl]acetamide obtained in the step 1, 3 ml of formic acid was added, and the mixture was stirred at room temperature for 24 hours. After the reaction was completed, formic acid was removed under reduced pressure.

Step 3

Preparation of N-[[(5S)-3-[4-(5-cyano-3,3a,4,6a-tetrahydro-1H-cyclopenta[c]pyrrol-2-yl)-3-fluorophenyl]-2-oxo-5-oxazolidiny]methyl]acetamide and hydrochloride thereof The concentrate obtained in the step 2 was dissolved in 2 ml of pyridine, the temperature was lowered to 0° C., and then, 0.1 ml (1.10 mmol) of phosphorous oxychloride was slowly added dropwise, and the mixture was stirred for 30 hours. After the reaction was completed, pyridine was removed under reduced pressure, water was added, and the mixture was extracted with methylene chloride, and then, the organic layer was dried over magnesium sulfate, filtered and concentrated under reduced pressure. The concentrate was separated by column chromatography using 3% (v/v) methanol-methylene chlrodie to obtain 38 mg (34%) of the title compound, of which NMR data is as follows.

$^1$H NMR (CDCl$_3$, 300 MHz) δ 7.39 (dd, J=15.1, 2.6 Hz, 1H), 7.05 (dd, J=8.7, 1.8 Hz, 1H), 6.72 (t, J=9.3 Hz, 1H), 6.52 (t, J=9.1 Hz, 1H), 4.77 (m, 1H), 4.02 (t, J=8.7 Hz, 1H), 3.77 (t, J=4.3 Hz, 1H), 3.63 (m, 3H), 3.38 (m, 3H), 3.22 (m, 2H), 3.13 (m, 1H), 2.59 (dd, J=16.2, 1.8 Hz, 1H), 2.01 (s, 3H)

$^{13}$C NMR (CDCl$_3$, 75 MHz) δ 171.50, 162.31, 155.21, 154.76, 151.96, 149.95, 133.90, 131.15, 117.62, 116.43, 115.10, 114.49, 108.11, 107.77, 72.19, 57.66, 54.25, 54.33, 50.73, 47.99, 42.20, 41.32, 39.63, 23.32

And, the obtained compound was treated with diethyl ether saturated with hydrogen chloride gas by the same method as the step 11 of the preparation example 1 to obtain hydrochloride thereof.

Example 4

Preparation of (5R)-3-[3-fluoro-4-(5-oxo-hexahydro-cyclopenta[c]pyrrol-2-yl)phenyl]-5-(1,2,3-triazol-1-ylmethyl)oxazolidin-2-one and hydrochloride thereof 5.0 g (12.39 mmol) of 2-[2-fluoro-4-[(5R)-5-(azidomethyl)-2-oxo-3-oxazolidinyl]phenyl]hexahydro-1H-spiro[cyclopenta[c]pyrrol-5,2'-[1,3]dioxolane] prepared in the step 9 of the preparation example 1 was dissolved in 100 ml of vinyl acetate, and the solution was heated to reflux for 30 hours. After the reaction was completed, water was added, and the mixture was extracted with ethyl acetate, and then, the organic layer was dried over magnesium sulfate, filtered and concentrated under reduced pressure. The concentrate was separated by column chromatography to obtain 2.5 g (47%) of 2-[2-fluoro-4-[(5R)-5-(1,2,3-triazol-1-ylmethyl)-2-oxo-3-oxazolidinyl]phenyl]hexahydro-1H-spiro[cyclopenta[c]pyrrol-5,2'-[1,3]dioxolane].

And then, 2.1 g (98%) of the title compound was obtained by the same method as the step 11 of the preparation example 1, except using 2.4 g (5.6 mmol) of the obtained 2-[2-fluoro-4-[(5s)-5-[(1,2,3-triazol-1-yl)methyl]-2-oxo-3-oxazolidinyl] phenyl]hexahydro-1H-spiro[cyclopenta[c]pyrrol-5,2'-[1,3] dioxolane] and 2.13 g (11.2 mmol) of p-toluene sulfonic acid hydrate, and the NMR data is as follows.

$^1$H NMR (CDCl$_3$, 300 MHz) δ 7.83 (d, J=1.2 Hz, 1H), 7.79 (d, J=1.2 Hz, 1H), 7.23 (dd, J=15.3, 2.4 Hz, 1H), 6.93 (dd, J=8.7, 2.7 Hz, 1H), 6.65 (t, J=9.3 Hz, 1H), 5.07 (m, 1H), 4.81 (dd, J=4.1, 1.4 Hz, 2H), 4.14 (t, J=9.0 Hz, 1H), 3.91 (dd, J=9.5, 6.1 Hz, 1H), 3.61 (m, 2H), 3.31 (m, 2H), 3.07 (m, 2H), 2.60 (dd, J=19.5, 9.0 Hz, 2H), 2.29 (m, 2H)

$^{13}$C NMR (CDCl$_3$, 75 MHz) δ 218.56, 153.71, 153.62, 134.27, 134.15, 134.02, 128.70, 128.57, 125.19, 115.96, 115.88, 115.04, 108.45, 108.10, 70.51, 55.85, 55.78, 52.09, 47.67, 43.29, 38.40

The obtained compound was treated with diethyl ether saturated with hydrogen chloride gas by the same method as the step 11 of the preparation example 1 to obtain hydrochloride thereof.

Example 5

Preparation of (5R)-3-[3-fluoro-4-(5-hydroxyimino-hexahydro-cyclopenta[c]pyrrol-2-yl)phenyl]-5-(1,2,3-triazol-1-ylmethyl)oxazolidin-2-one and hydrochloride thereof 100 mg (0.26 mmol) of (5R)-3-[3-fluoro-4-(5-oxo-hexahydro-cyclopenta[c]pyrrol-2-yl)phenyl]-5-(1,2,3-triazol-1-ylmethyl)oxazolidin-2-one obtained in the Example 4 was dissolved in 2 ml of distilled water, 24 mg (0.29 mmol) of sodium hydrogen carbonate and 27 mg (0.38 mmol) of hydroxyl amine hydrochloride were added, and the mixture was stirred at room temperature for 18 hours. After the reaction was completed, the reaction mixture was extracted with methylene chloride, and the organic layer was washed with a saturated aqueous solution of sodium chloride, dried over magnesium sulfate, filtered and concentrated under reduced pressure. The concentrate was separated by column chromatograpy using 4% (w/w) methanol-methylene chloride to obtain 20 mg (23%) of the title compound, of which NMR data is as follows.

$^1$H NMR (DMSO-$d_6$, 300 MHz) δ 10.36 (s, 1H), 8.18 (s, 1H), 7.78 (s, 1H), 7.32 (dd, J=16.1, 2.8 Hz, 1H), 7.04 (dd, J=8.9, 2.3 Hz, 1H), 6.75 (t, J=9.4 Hz, 1H), 5.10 (m, 1H), 4.83 (d, J=5.1 Hz, 2H), 4.18 (t, J=9.0 Hz, 1H), 3.83 (dd, J=9.3, 5.4 Hz, 1H), 3.47 (m, 2H), 3.10 (m, 2H), 2.83 (m, 2H), 2.63 (m, 2H), 2.27 (m, 2H)

The obtained compound was treated with diethyl ether saturated with hydrogen chloride gas by the same method as the step 11 of the preparation example 1 to obtain hydrochloride thereof.

Example 6

Preparation of (5R)-3-[3-fluoro-4-(5-methoxyimino-hexahydro-cyclopenta[c]pyrrol-2-yl)phenyl]-5-(1,2,3-triazol-1-ylmethyl)oxazolidin-2-one and hydrochloride thereof 100 mg (0.26 mmol) of (5R)-3-[3-fluoro-4-(5-oxo-hexahydro-cyclopenta[c]pyrrol-2-yl)phenyl]-5-(1,2,3-triazol-1-ylmethyl)oxazolidin-2-one obtained in the example 4 was dissolved in 2 ml of distilled water, 24 mg (0.29 mmol) of sodium hydrogen carbonate and 32 mg (0.39 mmol) of methoxyamine hydrochloride were added, and the mixture was stirred at room temperature for 48 hours. After the reaction was completed, the reaction mixture was extracted with methylene chloride, and the organic layer was washed with a saturated aqueous solution of sodium chloride, dried over magnesium sulfate, filtered and concentrated under reduced pressure. The concentrate was separated by column chromatography using 4% (v/v) methanol-methylene chloride to obtain 98 mg (92%) of the title compound, of which NMR data is as follows.

$^1$H NMR (DMSO-$d_6$, 300 MHz) δ 8.18 (d, J=0.9 Hz, 1H), 7.78 (d, J=1.2 Hz, 1H), 7.32 (dd, J=15.6, 2.4 Hz, 1H), 7.02 (dd, J=8.7, 2.1 Hz, 1H), 6.75 (t, J=9.3 Hz, 1H), 5.11 (m, 1H), 4.84 (d, J=4.8 Hz, 2H), 4.19 (t, J=9.3 Hz, 1H), 3.84 (dd, J=9.3, 6.0 Hz, 1H), 3.75 (s, 3H), 3.47 (m, 2H), 3.11 (m, 2H), 2.85 (m, 2H), 2.66 (m, 2H), 2.32 (m, 2H)

$^{13}$C NMR (DMSO-$d_6$, 75 MHz) δ 165.15, 154.28, 153.36, 150.18, 134.33, 129.62, 116.70, 115.64, 108.23, 107.90, 71.42, 61.61, 56.61, 56.34, 55.65, 52.50, 48.01, 35.51, 33.13

And, the obtained compound was treated with diethyl ether saturated with hydrogen chloride gas by the same method as the step 11 of the preparation example 1 to obtain hydrochloride thereof.

Example 7

Preparation of (5R)-3-[4-(5-cyanomethylene-hexahydro-cyclopenta[c]pyrrol-2-yl)-3-fluorophenyl]-5-(1,2,3-triazol-1-ylmethyl)oxazolidin-2-one and hydrochloride thereof 88 mg (83%) of the title compound was obtained by the same method as the example 1 except using 100 mg (0.26 mmol) of (5R)-3-[3-fluoro-4-(5-oxo-hexahydro-cyclopenta[c]pyrrol-2-yl)phenyl]-5-(1,2,3-triazol-1-ylmethyl)oxazolidin-2-one obtained in the example 4, 29 mg (0.26 mmol) of potassium tert-butoxide, and 230 mg (1.30 mmol) of diethyl cyanomethyl phosphonate, and the NMR data is as follows.

$^1$H NMR (CDCl$_3$, 300 MHz) δ 7.83 (s, 1H), 7.77 (s, 1H), 7.22 (dd, J=14.9, 1.6 Hz, 1H) 6.92 (dd, J=8.7, 2.4 Hz, 1H), 6.63 (t, J=9.3 Hz, 1H), 5.28 (t, 1H), 5.06 (m, 1H), 4.81 (dd, J=4.0, 1.4 Hz, 2H), 4.13 (t, J=9.0 Hz, 1H), 3.89 (dd, J=9.4, 6.1 Hz, 1H), 3.50 (m, 2H), 3.19 (m, 2H), 2.80 (m, 2H), 2.60 (m, 2H)

And, the obtained compound was treated with diethyl ether saturated with hydrogen chloride gas by the same method as the step 11 of the preparation example 1 to obtain hydrochloride thereof.

Example 8

Preparation of (5R)-3-[4-(5-cyanomethyl-3,3a,4,6a-tetrahydro-1H-cyclopenta[c]pyrrol-2-O-3-fluorophenyl]-5-(1,2,3-triazol-1-ylmethyl)oxazolidin-2-one and hydrochloride thereof 37 mg (35%) of the title compound was obtained by the same method as the example 2, except using 100 mg (0.26 mmol) of (5R)-3-[3-fluoro-4-(5-oxo-hexahydro-cyclopenta[c]pyrrol-2-yl)phenyl]-5-(1,2,3-triazol-1-ylmethyl)oxazolidin-2-one obtained in the example 4, 2 mg (0.03 mmol) of ammonium acetate, and 22 mg (0.26 mmol) of cyanoacetic acid, and the NMR data is as follows.

$^1$H NMR (CD$_3$OD, 300 MHz) δ 8.10 (d, J=1.2 Hz, 1H), 7.79 (d, J=1.2 Hz, 1H), 7.30 (dd, J=15.0, 2.4 Hz, 1H), 7.02 (dd, J=9.0, 2.7, 1H), 6.84 (t, J=9.0 Hz, 1H), 5.69 (d, J=2.4 Hz, 1H), 5.14 (m, 1H), 4.90 (m, 2H), 4.25 (t, J=9.3 Hz, 1H), 3.96 (dd, J=9.3, 5.4 Hz, 1H), 3.49 (m, 1H), 3.39-3.08 (m, 6H), 2.78 (dd, J=16.5, 8.1 Hz, 1H), 2.32 (d, J=16.8, 1.5 Hz, 1H)

$^{13}$C NMR (CD$_3$OD, 75 MHz) δ 156.09, 152.88, 135.88, 135.75, 135.23, 134.58, 131.81, 131.68, 131.54, 129.51, 127.25, 118.77, 118.57, 118.50, 116.27, 109.21, 108.86, 72.57, 59.09, 59.03, 56.41, 56.34, 53.47, 50.74, 42.42, 41.46

And, the obtained compound was treated with diethyl ether saturated with hydrogen chloride gas by the same method as the step 11 of the preparation example 1 to obtain hydrochloride thereof.

Example 9

Preparation of (5R)-3-[4-(5-cyano-3,3a,4,6a-tetrahydro-1H-cyclopenta[c]pyrrol-2-yl)-3-fluorophenyl]-5-(1,2,3-triazol-1-ylmethyl)oxazolidin-2-one and hydrochloride thereof

Step 1

Preparation of (5R)-3-[4-(5-cyano-5-trimethylsilanyloxy-hexahydro-cyclopenta[c]pyrrol-2-yl)-3-fluorophenyl]-5-(1,2,3-triazol-1-ylmethyl)oxazolidin-2-one 194 mg (51%) of (5R)-3-[4-(5-cyano-5-trimethylsilanyloxy-hexahydro-cyclopenta[c]pyrrol-2-yl)-3-fluorophenyl]-5-(1,2,3-triazol-1-ylmethyl)oxazolidin-2-one was obtained by the method as the step 1 of the example 3, except using 300 mg (0.78 mmol) of (5R)-3-[3-fluoro-4-(5-oxo-hexahydro-cyclopenta[c]pyrrol-2-yl)phenyl]-5-(1,2,3-triazol-1-ylmethyl)oxazolidin-2-one obtained in the example 4, 30 mg (0.09 mmol) of indium tribromide, and 348 mg (3.50 mmol) of trimethylsilyl cyanide.

Step 2

Preparation of (5R)-3-[4-(5-cyano-3,3a,4,6a-tetrahydro-1H-cyclopenta[c]pyrrol-2-yl)-3-fluorophenyl]-5-(1,2,3-triazol-1-ylmethyl)oxazolidin-2-one hydrochloride thereof 43 mg (48%) of the title compound was obtained by the same method as the step 2 and step 3 of the example 3, except using 110 mg (0.23 mmol) of (5R)-3-[4-(5-cyano-5-trimethylsilanyloxy-hexahydro-cyclopenta[c]pyrrol-2-yl)-3-fluorophenyl]-5-(1,2,3-triazol-1-ylmethyl)oxazolidin-2-one obtained in the step 1, and 184 mg (1.20 mmol) of phosphorous oxychlrodie, and the NMR data is as follows.

$^1$H NMR (CDCl$_3$, 300 MHz) δ 7.82 (d, J=1.2 Hz, 1H), 7.25 (dd, J=14.9, 2.2 Hz, 1H), 6.94 (dd, J=8.9, 2.9 Hz, 1H), 6.69 (t, J=9.1 Hz, 1H), 5.06 (m, 1H), 4.80 (m, 2H), 4.13 (t, J=9.0 Hz, 1H), 3.89 (dd, J=9.4, 6.1 Hz, 1H), 3.39 (m, 1H), 3.21 (m, 3H), 3.21 (m, 2H), 3.12 (m, 1H), 2.58 (dd, J=16.5, 2.1 Hz, 1H)

$^{13}$C NMR (CDCl$_3$, 75 MHz) δ 155.07, 153.78, 151.83, 149.95, 134.73, 130.38, 125.36, 117.61, 117.53, 116.43, 115.09, 114.97, 114.92, 108.48, 108.14, 70.64, 57.65, 57.60, 54.27, 54.19, 52.30, 50.72, 47.76, 41.31, 39.62

And, the obtained compound was treated with diethyl ether saturated with hydrogen chloride gas by the same method as the step 11 of the preparation example 1 to obtain hydrochloride thereof.

Experimental Example 1

In Vitro Antibacterial Activity Test

For in vitro antibacterial activities of the compounds prepared in Examples 1 to 9, according to Agar Dilution method using Mueller Hinton Agar (LeClercq R, et al., N Engl J Med 1988, 319, 157-161.), strains in the following Table 1 (those obtained from infectious patients, provided by Infection Control in Yonsei University, Korea) were cultured at 37° C. for 18 hours, and then, diluted by stages two times, and inoculated plates were arranged in line and visually observed to determine minimum inhibitory concentration (MIC, μg/mL) of the title compounds. As control substance, linezolid (Zyvox, Pharmacia & Upjohn) was used.

The strains used in the experimental example and the results are summarized in the following Table 1.

TABLE 1

| 화합물 번호 | A | B |
|---|---|---|
| 1 | O=[cyclopentapyrrole] | NHAc |
| 2 | HON=[cyclopentapyrrole] | NHAc |
| 3 | H$_3$CON=[cyclopentapyrrole] | NHAc |
| 4 | NC-CH=[cyclopentapyrrole] | NHAc |
| 5 | NC-CH$_2$-[cyclopentenopyrrole] | NHAc |
| 6 | NC-[cyclopentenopyrrole] | NHAc |
| 7 | O=[cyclopentapyrrole] | 1,2,3-triazol-1-yl |
| 8 | HON=[cyclopentapyrrole] | 1,2,3-triazol-1-yl |
| 9 | H$_3$CON=[cyclopentapyrrole] | 1,2,3-triazol-1-yl |
| 10 | NC-CH=[cyclopentapyrrole] | 1,2,3-triazol-1-yl |
| 11 | NC-CH$_2$-[cyclopentenopyrrole] | 1,2,3-triazol-1-yl |

TABLE 1-continued

| 화합물 번호 | A | B |
|---|---|---|
| 12 | 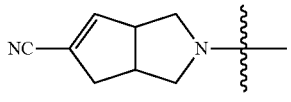 | 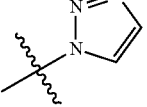 |

Results of experiment of antibacterial activities of the compounds (MIC, μg/mL)

| Strains | 1 | 2 | 3 | 4 | 5 | 6 | 7 | 8 | 9 | LZD |
|---|---|---|---|---|---|---|---|---|---|---|
| Staphylococcus aureus[1] | 3.1 | 1.5 | 1.5 | 3.1 | 6.2 | 6.2 | 0.7 | 1.5 | 1.5 | 3.1 |
| Staphylococcus aureus[2] | 3.1 | 3.1 | 3.1 | 3.1 | 6.2 | 6.2 | 1.5 | 6.2 | 3.1 | 3.1 |
| Coagulase negative staphylococci[1] | 3.1 | 3.1 | 3.1 | 3.1 | 6.2 | 6.2 | 1.5 | 6.2 | 3.1 | 3.1 |
| Coagulase negative staphylococci[2] | 3.1 | 3.1 | 3.1 | 3.1 | 6.2 | 6.2 | 1.5 | 6.2 | 3.1 | 3.1 |
| Enterococcus faecalis[3] | 1.5 | 3.1 | 3.1 | 1.5 | 6.2 | 3.1 | 3.1 | 6.2 | 3.1 | 1.5 |
| Enterococcus faecalis[4] | 1.5 | 1.5 | 3.1 | 1.5 | 6.2 | 1.5 | 1.5 | 6.2 | 3.1 | 1.5 |
| Enterococcus faecium[3] | 1.5 | 1.5 | 1.5 | 3.1 | 6.2 | 1.5 | 1.5 | 6.2 | 3.1 | 1.5 |
| Enterococcus faecium[4] | 0.7 | 1.5 | 1.5 | 1.5 | 3.1 | 1.5 | 1.5 | 6.2 | 3.1 | 1.5 |
| Staphylococcus pneumoniae[5] | 0.7 | 0.7 | 0.3 | 0.3 | 0.7 | 0.1 | 0.3 | 1.5 | 0.7 | 0.7 |
| Staphylococcus pneumoniae[6] | 0.7 | 0.7 | 0.7 | 0.7 | 1.5 | 0.3 | 0.7 | 3.1 | 1.5 | 0.7 |
| Staphylococcus pyogenes | 0.7 | 0.7 | 0.7 | 0.3 | 0.7 | 0.1 | 0.3 | 1.5 | 0.7 | 0.7 |
| Staphylococcus agalactiae | 1.5 | 1.5 | 1.5 | 0.7 | 1.5 | 0.3 | 0.7 | 3.1 | 1.5 | 1.5 |
| Haemophilus influenzae[7] | 0.7 | 1.5 | 0.3 | 1.5 | 3.1 | 0.3 | 0.3 | 1.5 | 0.7 | 0.7 |

LZD: linezolid (Zybox ™)
1~7 indicated in the strains denote as follows.
[1] methicillin resistant
[2] methicillin susceptible
[3] vancomycin resistant
[4] vancomycin susceptible
[5] penicillin non-susceptible
[6] penicillin susceptible
[7] beta-lactamase-positive As shown in the Table 1, it is confirmed that novel oxazolidinone derivative containing a bycyclic cyclopenta[c]pyrrolyl group prepared according to the Examples of the present invention have high antibacterial effects against various strains such as Staphylococcus sp. including Staphylococcus aureus and Staphylococcus pneumonia, Enterococcus sp. and Haemophilus influenza, and the like. Particularly, the compounds of the Examples 2, 3, 4 and 7 exhibit high antibacterial activities.

Experimental Example 2

In Vitro Antituberculous Activity Test

Minimum inhibitory concentration (MIC, μg/mL) of each compound against vancomycin-resistant strain (Mycobacterium tuberculosis (Mtb)) H37Rv (Gene bank in Seoul Women's University, Korea) was measured by Microplate method using Alamar Blue Assay (Collins, L. et al., (1997), Antimicrobial Agents and Chemotherapy, 41, 1004-1009).

Specifically, Mtb was cultured in 10 mL of Middlebrook 7H9 medium (Difco, Sparks. MD) supplemented with 0.2% (v/v) glycerol (Sigma Chemical Co., SaintLouis, Mo.), Casitone 1.0 g/L (Difco), 10% (v/v) OADC (oleicacid, albumin, dextrose, catalase; Difco), and 0.05% (v/v) Tween80 (Sigma), at 15 to 45° C., such that optical density may become 0.4 at 600 nm.

The initial dimethylsulfoxide solutions (10 mg/mL) of the compounds prepared in the examples were prepared, and solutions two times continuously diluted to 7H9 medium were prepared on a microplate. The medium was diluted to 1:50, and mixed to 2×10$^5$ CFU/mL on a plate wall.

The plate containing the compound diluent and Mtb was cultured at 37° C. for 7 days, 20 μL of 10× Alamar blue solution (Serotec, Raleigh, N.C.) was added to each well. After culturing for 24 hours, color change from pink to blue was measured, and the lowest concentration for inhibiting color change was determined as minimum inhibitory concentration (MIC, μg/mL), which is shown in the following Table 2.

TABLE 2

Results of experiment of antituberculous activities of the compounds (MIC, μg/mL)

| | Microplate Alamar Blue test result (MIC, μg/mL) Test compound | | | | | | | | |
|---|---|---|---|---|---|---|---|---|---|
| Test bacteria | 1 | 2 | 3 | 4 | 6 | 7 | 8 | 9 | LZD |
| Mycobacterium tuberculosis (Yonsei Univ, Korea) | 1 | 1 | 0.5 | 0.5 | 1 | 1 | 2 | 1 | 1 |

As shown in the Table 2, novel oxazolidinone derivative containing a bicyclic cyclopenta[c]pyrrolyl group prepared according to the examples of the present invention exhibit 0.5 to 2 minimum inhibitory concentration (MIC, μg/mL) against vancomycin-resistant tuberculous strain, and thus has excellent antituberculous effects. Particularly, the compounds of the examples 1, 2, 6, 7 and 9 exhibit antibacterial effects equivalent to linezolid, and the compounds of the examples 3 and 4 exhibit more excellent antibacterial activities than linezolid.

Experimental Example 3

In Vitro Toxicity and Stability Test

In vitro toxicity and stability test was additionally conducted for the compound of the Example 4 which exhibited excellent antibacterial activity in the Experimental Example 2, and the results are shown in the following Table 3. CYP450 remaining test was conducted using Vivid® CYP450 Screening Kits Protocol (Invitrogen), and hERG assay for cardiac toxicity test was conducted using an automated patch-clamp device, NPC-16 Patchliner (Nanion Technologies, Munchen, Germany) according to the method of C. Farre, et al. (Combinatorial Chemistry & High Throughput Screening, 2009, 12, 24-37). And, human hepatic microsomal stability test was conducted according to the method of W. A. Korfmacher, et al. (Rapid Commun. Mass Spectrom. 13, 901-907 (1999)).

TABLE 3

|  | CYP450 Remaining activity (%) | | | | hERG | | Human Hepatic Microsomal stability Remaining activity after 30 minutes |
| --- | --- | --- | --- | --- | --- | --- | --- |
|  | 1A2 | 2D6 | 2C9 | 3A4 | IC$_{50}$ (μM) | Max, | (%) |
| Positive control | 2.3[1] | 11.1[2] | −3.5[3] | 2.3[4] |  |  |  |
| Example 4 | 94.9 | 107.7 | 73.7 | 105.6 | 80.5 ± 6.03 | 38% | 83.8% |

Positive controls 1-4 are as follows.
[1]a-naphthoflavon,
[2]quinidine,
[3]sulfaphenazol,
[4]ketoconazole, As shown in the Table 3, the compound of the Example 4 exhibits remaining activities of minimum 73.6%, maximum 105.6% in the activity test for 4 isozymes of CYP450 (1A2, 2D6, 2C9, 3A4), indicating that it is not affected by CYP450 compared to positive control. And, the compound exhibits very high stability of remaining activity of 83.8% after 30 minutes in human hepatic microsomal stability test. And, the compound 4 does not have hERG bonding in the in vitro hERG bonding assay, which is a pilot experiment of cardiac toxicity, confirming that it is very stable in terms of cardiac toxicity.

As explained, novel oxazolidinone derivative of the present invention exhibits excellent activity against MRSA and other gram positive bacteria compared to control, linezolid (Upjohn). Particularly, it exhibits equivalent or two times more excellent activity against tuberculosis strain (*Mycobacterium tuberculosis*). And, it is confirmed that the compound has very excellent stability in terms of in vitro toxicity and stability, and thus, it may be useful for an antibacterial agent, antibiotics, or a pharmaceutical composition for treatment of infectious disease caused by the pathogen, and the like.

What is claimed is:

1. An oxazolidinone derivative containing a cyclopenta[c]pyrrolylphenyl group, and represented by the following Chemical Formula 1, or a pharmaceutically acceptable salt thereof:

[Chemical Formula 1]

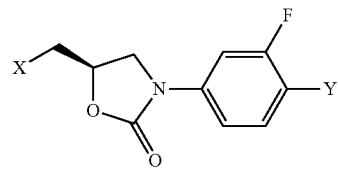

wherein,

X is acetamido (-NHAc) group or 1H-1,2,3-triazol-1-yl group, when X is acetamido (-NHAc) group, Y is

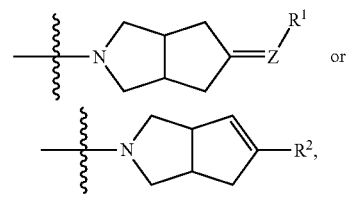

Z is nitrogen or carbon, when Z is nitrogen, $R^1$ is cyano group (—CN), and when Z is carbon, $R^1$ is hydroxyl group (—OH), $C_1$-$C_7$ alkyloxy group, benzyloxy group, or cyano group (—CN), and $R^2$ is cyano group or cyanomethyl group; and when X is 1H-1,2,3-triazol-1-yl group, Y is

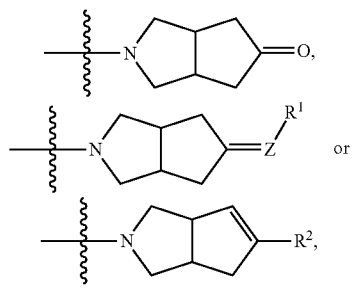

Z is nitrogen or carbon, $R^1$ is hydroxyl group (—OH), $C_1$-$C_7$ alkyloxy group, benzyloxy group, cyano group (—CN), or $C_1$-$C_7$ alkyloxycarbonyl group, and $R^2$ is cyano group or cyanomethyl group.

2. The oxazolidinone derivative or a pharmaceutically acceptable salt thereof according to claim 1, wherein the oxazolidinone derivative of the Chemical Formula 1 is selected from the group consisting of compounds of the following Chemical Formula 2a, Chemical Formula 7a and Chemical Formulae 8 to 10,

[Chemical Formula 2a]

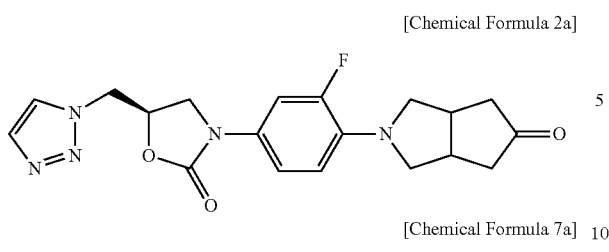

[Chemical Formula 7a]

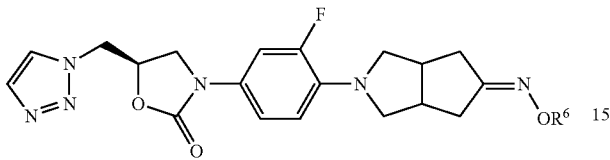

wherein, $R^6$ is hydrogen, $C_1$-$C_7$ alkyl group, or benzyl group;

[Chemical Formula 8]

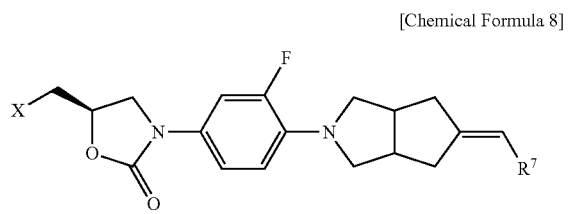

[Chemical Formula 9]

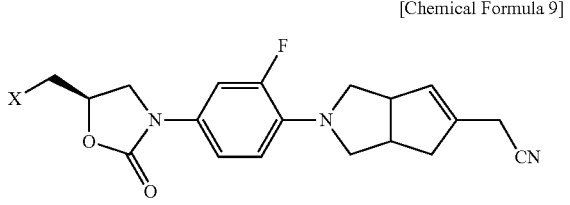

[Chemical Formula 10]

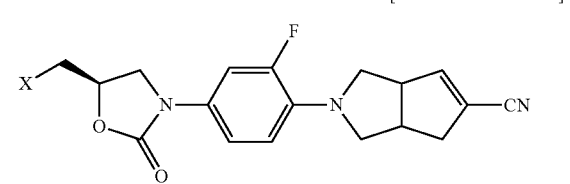

Wherein, Chemical Formulae 8 to 10,

X is acetamido (-NHAc) group or 1H-1,2,3-triazol-1-yl group, $R^7$ is cyano group, or $C_1$-$C_7$ alkyloxycarbonyl group.

3. The oxazolidinone derivative or a pharmaceutically acceptable salt thereof according to claim 1, wherein the pharmaceutically acceptable salt is selected from the group consisting of hydrochloride, hydrobromide, methanesulfonate, hydroxyethansulfonate, sulfate, acetate, trifluoroacetate, maleate, benzenesulfonate, toluenesulfonate, nitrate, phosphate, borate, tartrate, citrate, succinate, benzoate, ascorbate and salicylate.

4. The oxazolidinone derivative or a pharmaceutically acceptable salt thereof according to claim 1, wherein the oxazolidinone derivative of the Chemical Formula 1 is selected from the group consisting of the following compounds 1) to 9):

1) N-[[(5S)-3-[4-(5-cyanomethylene-hexahydro-cyclopenta[c]pyrrol-2-yl)-3-fluorophenyl]-2-oxo-5-oxazolidinyl]methyl]acetamide;

2) N-[[(5S)-3-[4-(5-cyanomethyl-3,3a,4,6a-tetrahydro-1H-cyclopenta[c]pyrrol-2-yl)-3-fluorophenyl]-2-oxo-5-oxazolidinyl]methyl]acetamide;

3) N-[[(5S)-3-[4-(5-cyano-3,3a,4,6a-tetrahydro-1H-cyclopenta[c]pyrrol-2-yl)-3-fluorophenyl]-2-oxo-5-oxazolidinyl]methyl]acetamide;

4) (5R)-3-[3-fluoro-4-(5-oxo-hexahydro-cyclopenta[c]pyrrol-2-yl)phenyl]-5-(1,2,3-triazol-1-ylmethyl)oxazolidin-2-one;

5) (5R)-3-[3-fluoro-4-(5-hydroxyimino-hexahydro-cyclopenta[c]pyrrol-2-yl)phenyl]-5-(1,2,3-triazol-1-ylmethyl)oxazolidin-2-one;

6) (5R)-3-[3-fluoro-4-(5-methoxyimino-hexahydro-cyclopenta[c]pyrrol-2-yl)phenyl]-5-(1,2,3-triazol-1-ylmethyl)oxazolidin-2-one;

7) (5R)-3-[4-(5-cyanomethylene-hexahydro-cyclopenta[c]pyrrol-2-yl)-3-fluorophenyl]-5-(1,2,3-triazol-1-ylmethyl)oxazolidin-2-one;

8) (5R)-3-[4-(5-cyanomethyl-3,3a,4,6a-tetrahydro-1H-cyclopenta[c]pyrrol-2-yl)-3-fluorophenyl]-5-(1,2,3-triazol-1-ylmethyl)oxazolidin-2-one; and 9) (5R)-3-[4-(5-cyano-3,3a,4,6a-tetrahydro-1H-cyclopenta[c]pyrrol-2-yl)-3-fluorophenyl]-5-(1,2,3-triazol-1-ylmethyl)oxazolidin-2-one.

5. A pharmaceutical composition comprising the oxazolidinone derivative or a pharmaceutically acceptable salt thereof according to claim 1 as an active ingredient.

6. An antibacterial composition comprising the oxazolidinone derivative or a pharmaceutically acceptable salt thereof according to claim 1 as an active ingredient.

7. The antibacterial composition according to claim 6, wherein the composition has an antibacterial activity against at least one bacteria selected from the group consisting of *Staphylococcus* sp., *Enterococcus* sp., *Escherichia coli*, *Bacillus* sp., *Salmonella* sp., and *Mycobacterium* sp.

8. The antibacterial composition according to claim 7, wherein the bacteria has resistance to methicillin or vancomycin.

9. A method for treating an infectious disease caused by a pathogen, comprising administering a therapeutically effective amount of the oxazolidinone derivative or a pharmaceutically acceptable salt thereof according to claim 1 to a patient in need thereof.

10. The method according to claim 9, wherein the pathogen is at least one bacteria selected from the group consisting of *Staphylococcus* sp., *Enterococcus* sp., *Escherichia coli*, *Bacillus* sp., *Salmonella* sp., and *Mycobacterium* sp.

11. The method according to claim 10, wherein the pathogen has resistance to methicillin or vancomycin.

12. The method according to claim 9, wherein the therapeutically effective amount is 0.01 mg/kg to 100 mg/kg a day.

13. The method according to claim 9, wherein the administration is conducted by oral, intravenous, intramuscular, or subcutaneous injection.

* * * * *